(12) United States Patent
Yamazaki

(10) Patent No.: US 8,450,683 B2
(45) Date of Patent: May 28, 2013

(54) IMAGE PROCESSING APPARATUS, AN IMAGE GENERATING METHOD, AND A SYSTEM

(75) Inventor: Takashi Yamazaki, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 13/537,940

(22) Filed: Jun. 29, 2012

(65) Prior Publication Data
US 2013/0043386 A1    Feb. 21, 2013

(30) Foreign Application Priority Data

Aug. 17, 2011 (JP) ................................. 2011-178330

(51) Int. Cl.
*H01J 37/28* (2006.01)
(52) U.S. Cl.
CPC ....................................... *H01J 37/28* (2013.01)
USPC ........................... 250/306; 250/307; 250/311
(58) Field of Classification Search
USPC ......................................... 250/306, 307, 311
See application file for complete search history.

(56) References Cited

U.S. PATENT DOCUMENTS 5,866,905 A * 2/1999 Kakibayashi et al. ........ 250/311
6,992,286 B2 * 1/2006 Yaguchi et al. ............... 250/306

FOREIGN PATENT DOCUMENTS
JP    2009-514141    4/2009
JP    2010-257883    11/2010
WO   WO-2005/006384  1/2005

OTHER PUBLICATIONS

S. J. Pennycook et. al., "High-Resolution Incoherent Imaging of Crystals," The American Physical Society (Feb. 19, 1990), pp. 938-941.
S. D. Findlay et. al., "Robust atomic resolution imaging of light elements using scanning transmission electron microscopy," American Institute of Physics (Nov. 13, 2009), pp. 191913-1 to 191913-3.
K. Watanabe et. al., "Lattice imaging in low-angle and high-angle bright-field scanning transmission electron microscopy," International Union of Crystallography (2004), pp. 591-597.

* cited by examiner

*Primary Examiner* — Kiet T Nguyen
(74) *Attorney, Agent, or Firm* — Fujitsu Patent Center

(57) ABSTRACT

The method disclosed in this specification includes: acquiring a dark-field image produced by capturing an image of a sample with a scanning transmission electron microscope by detecting electrons scattered at angles between a first angle to the optical axis of the scanning transmission electron microscope and a second angle which is larger than the first angle; acquiring a bright-field image captured simultaneously with the dark-field image by detecting electrons scattered within a third angle which is smaller than the first angle; generating a reverse image by reversing lightness and darkness of the dark-field image; and generating a difference image each of whose pixels has a brightness value equal to the difference between the brightness of the corresponding pixel in the reverse image and the brightness of the corresponding pixel in the bright-field image.

9 Claims, 18 Drawing Sheets

FIG.9

BRIGHT-FIELD IMAGE CAPTURED USING HIGH-ANGLE BRIGHT-FIELD IMAGE DETECTOR — BRIGHT-FIELD IMAGE CAPTURED USING LOW-ANGLE BRIGHT-FIELD IMAGE DETECTOR = BRIGHT-FIELD IMAGE CAPTURED USING HIGH-ANGLE ANNULAR BRIGHT-FIELD IMAGE DETECTOR

⇐

REVERSE IMAGE GENERATED BY REVERSING LIGHTNESS AND DARKNESS OF DARK-FIELD IMAGE CAPTURED USING HIGH-ANGLE ANNULAR DARK-FIELD IMAGE DETECTOR

FIG.10
(A) 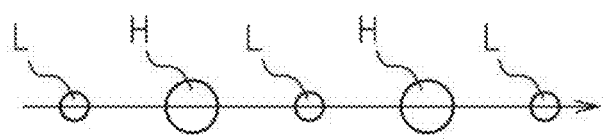
(B) 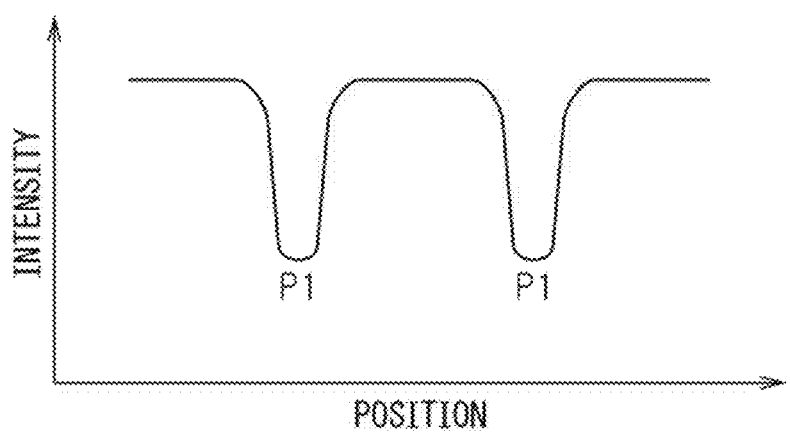
(C) 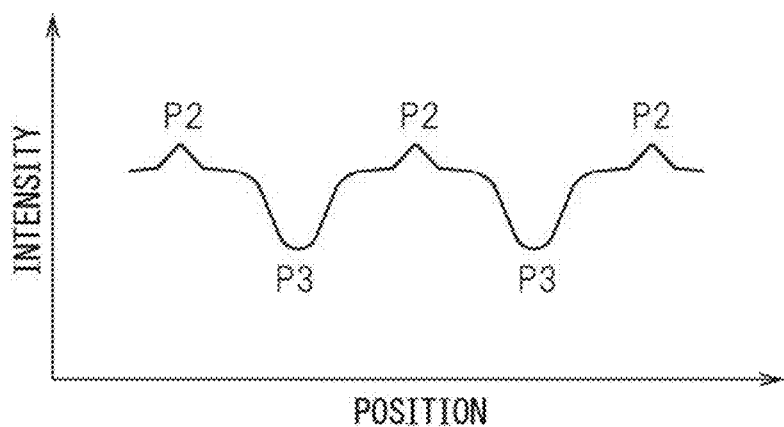
(D) 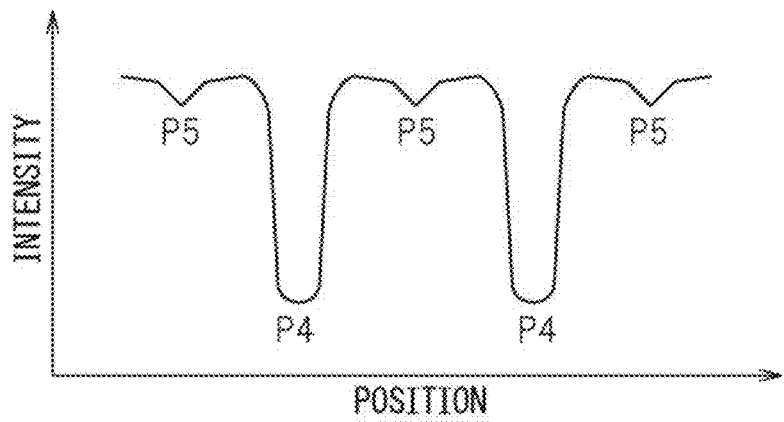

FIG.19
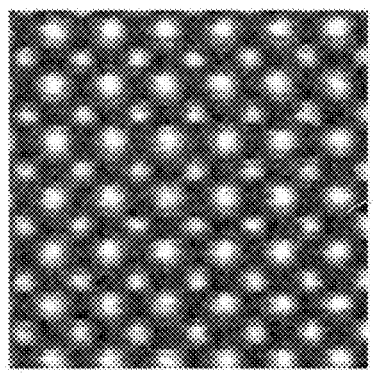
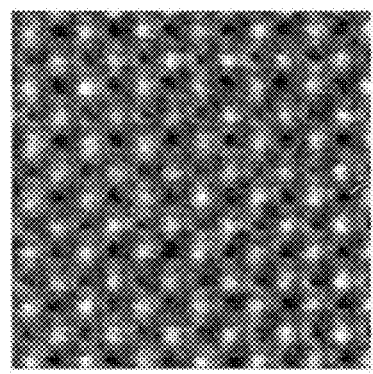
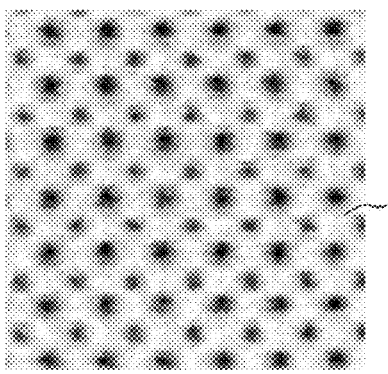
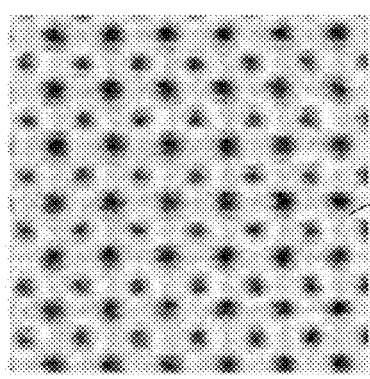
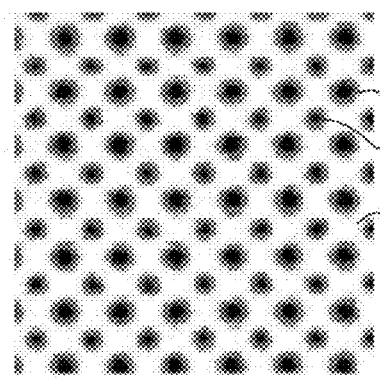
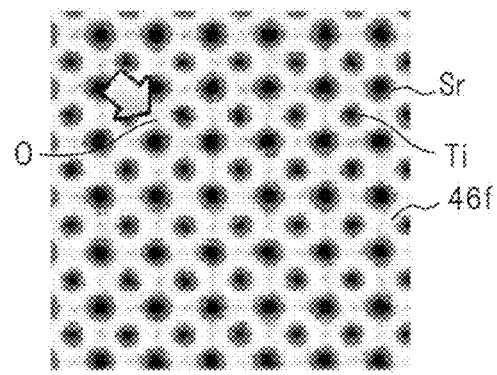

IMAGE PROCESSING APPARATUS, AN IMAGE GENERATING METHOD, AND A SYSTEM

CROSS-REFERENCE TO RELATED APPLICATIONS

This application is based upon and claims the benefit of priority of the prior Japanese Patent Application No. 2011-178330, filed on Aug. 17, 2011, the entire contents of which are incorporated herein by reference.

FIELD

The present invention relates to an image processing apparatus, an image generating method, and a system.

BACKGROUND

A scanning transmission electron microscope is used to analyze the structure of a material. In the scanning transmission electron microscope, the surface of a sample is scanned with a convergent electron beam, and the arrangement of atoms can be observed with high resolution by detecting the electrons transmitted through the sample.

FIG. 1 is a diagram schematically illustrating a scanning transmission electron microscope according to a prior art example.

The electron beam B entering the sample S along the optical axis of the electron microscope passes through the sample S where the electrons are scattered by the atoms composing the sample S. Then, electrons that have been scattered at high angles with respect to the optical axis are detected by an annular first detector 126. While the surface of the sample S is being scanned with the convergent electron beam B, the electrons scattered at high angles are detected by the first detector 126 on a per-scan basis, and a dark-field image of the sample S is obtained by converting the detected signal into a visible image as a function of the scanning position of the electron beam.

The electrons scattered at high angles by the sample S and detected by the first detector 126 are those scattered primarily by thermal diffuse scattering by the atoms composing the sample S. The scattering center of the thermal diffuse scattering is the atomic center, and its scattering intensity increases with increasing atomic number. The method of capturing a dark-field image using a scanning transmission electron microscope in this manner is called HAADF-STEM (High-Angle Annular Dark-Field Scanning Transmission Electron Microscopy).

Electrons scattered at smaller angles than the electrons detected by the first detector 126 are detected using a circular second detector 127. A bright-field image is obtained by converting the signal detected by the second detector 127 into a visible image. In this way, using the scanning transmission electron microscope, not only a dark-field image but also a bright-field image can be captured.

With the above HAADF-STEM method, high-resolution atomic images can be obtained since the captured atomic images are not sensitive to the defocus value nor are they sensitive to the thickness of the sample. Furthermore, since the brightness of the atomic image appearing at each atomic position depends on the atomic number, heavier atoms having higher atomic numbers are easier to detect.

On the other hand, with the HAADF-STEM method, it may be difficult to detect light atoms having low atomic numbers, because in that case the number of electrons scattered by thermal diffuse scattering is small. In particular, in the case of a sample containing heavy atoms and light atoms having different atomic numbers, it is difficult to capture images of such heavy atoms and light atoms with good contrast.

In view of this, a method has been proposed that captures images of heavy atoms and light atoms with good contrast by using a scanning transmission electron microscope.

FIG. 2 is a diagram schematically illustrating a scanning transmission electron microscope according to another prior art example.

The scanning transmission electron microscope depicted in FIG. 2 includes an annular detector 129 for detecting electrons. The annular detector 129 is similar in structure to the first detector 127 depicted in FIG. 1, except that the former has a vacant circular center.

By capturing a bright-field image using the annular detector 129 depicted in FIG. 2, good contrast images of heavy atoms and light atoms can be captured simultaneously.

Japanese Laid-open Patent Publication No. 2010-257883
Japanese Laid-open Patent Publication No. 2009-514141
Non-patent literature, S. J. Pennycook, et al., Phys. Rev. Lett. 64 (1990)938
Non-patent Publication, S. D. Findlay, et al., App. Phy. Lett. 95 (2009)191913

SUMMARY

Usually, a scanning transmission electron microscope employing the HAADF-STEM method includes, as illustrated in FIG. 1, an annular first detector 126 for capturing a dark-field image and a circular detector 127 for capturing a bright-field image. However, the conventional scanning transmission electron microscope does not have an annular detector 129 such as depicted in FIG. 2 for capturing a bright-field image.

In view of this, it is proposed to provide such an annular detector in the conventional scanning transmission electron microscope by using a circular shield plate so as to cover the center portion of the second detector 127 depicted in FIG. 1.

However, if such a shield plate is to be added in the scanning transmission electron microscope, the entire system has to be modified accordingly. Furthermore, since capturing an image of a sample with a shield plate placed so as to cover the center portion of the second detector 127 depicted in FIG. 1 requires a new imaging technique, it is expected that, with the imaging technique employed in the conventional scanning transmission electron microscope, it is difficult to capture an image by using such a shield plate.

According to an aspect of the embodiment disclosed in this specification, an image generating method including: acquiring a dark-field image produced by capturing an image of a sample with a scanning transmission electron microscope by detecting electrons scattered at angles between a first angle to the optical axis of the scanning transmission electron microscope and a second angle which is larger than the first angle; acquiring a bright-field image captured simultaneously with the dark-field image by detecting electrons scattered within a third angle which is smaller than the first angle; generating a reverse image by reversing lightness and darkness of the dark-field image; and generating a difference image each of whose pixels has a brightness value equal to the difference between the brightness of the corresponding pixel in the reverse image and the brightness of the corresponding pixel in the bright-field image is provided.

According to an aspect of the embodiment disclosed in this specification, an image processing apparatus including: an input unit which takes as inputs a dark-field image produced by capturing an image of a sample with a scanning transmission electron microscope by detecting electrons scattered at angles between a first angle to the optical axis of the scanning transmission electron microscope and a second angle which is larger than the first angle, and a bright-field image captured simultaneously with the dark-field image by detecting electrons scattered within a third angle which is smaller than the first angle; and an image processing unit which generates a reverse image by reversing lightness and darkness of the dark-field image, and generates a difference image each of whose pixels has a brightness value equal to the difference between the brightness of the corresponding pixel in the reverse image and the brightness of the corresponding pixel in the bright-field image is also provided.

Further, according to an aspect of the embodiment disclosed in this specification, a system including: a scanning transmission electron microscope which includes an electron source which emits an electron beam, an objective lens by which the electron beam emitted from the electron source is converged onto a sample, a scanning coil, disposed between the electron source and the objective lens, for scanning the electron beam across a surface of the sample, a focusing lens by which the electron beam transmitted through the sample is focused to a spot, a first detector for detecting electrons scattered at angles between a first angle to the optical axis of the scanning transmission electron microscope and a second angle which is larger than the first angle, a second detector for detecting electrons scattered within a third angle which is smaller than the first angle, and an image generating unit which generates a dark-field image based on a detection signal supplied from the first detector and a bright-field image based on a detection signal supplied from the second detector; and an image processing apparatus which includes an input unit which takes the dark-field image and the bright-field image as inputs, and an image processing unit which generates a reverse image by reversing lightness and darkness of the dark-field image, and generates a difference image each of whose pixels has a brightness value equal to the difference between the brightness of the corresponding pixel in the reverse image and the brightness of the corresponding pixel in the bright-field image is provided.

The object and advantages of the embodiments will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 9 is a diagram (part 3) illustrating the concept of image processing for generating an electron micrograph image on which both heavy atoms and light atoms can be observed simultaneously.

FIG. 10 is a diagram (part 4) illustrating the concept of image processing for generating an electron micrograph image on which both heavy atoms and light atoms can be observed simultaneously.

FIG. 19 is a diagram illustrating an example of difference image generation.

DESCRIPTION OF EMBODIMENT

One preferred embodiment of a system disclosed in this specification will be described below with reference to drawings. It will, however, be noted that the technical scope of the present invention is not limited to the specific embodiments described herein but extends to the inventions described in the appended claims and their equivalents.

Figure 3:
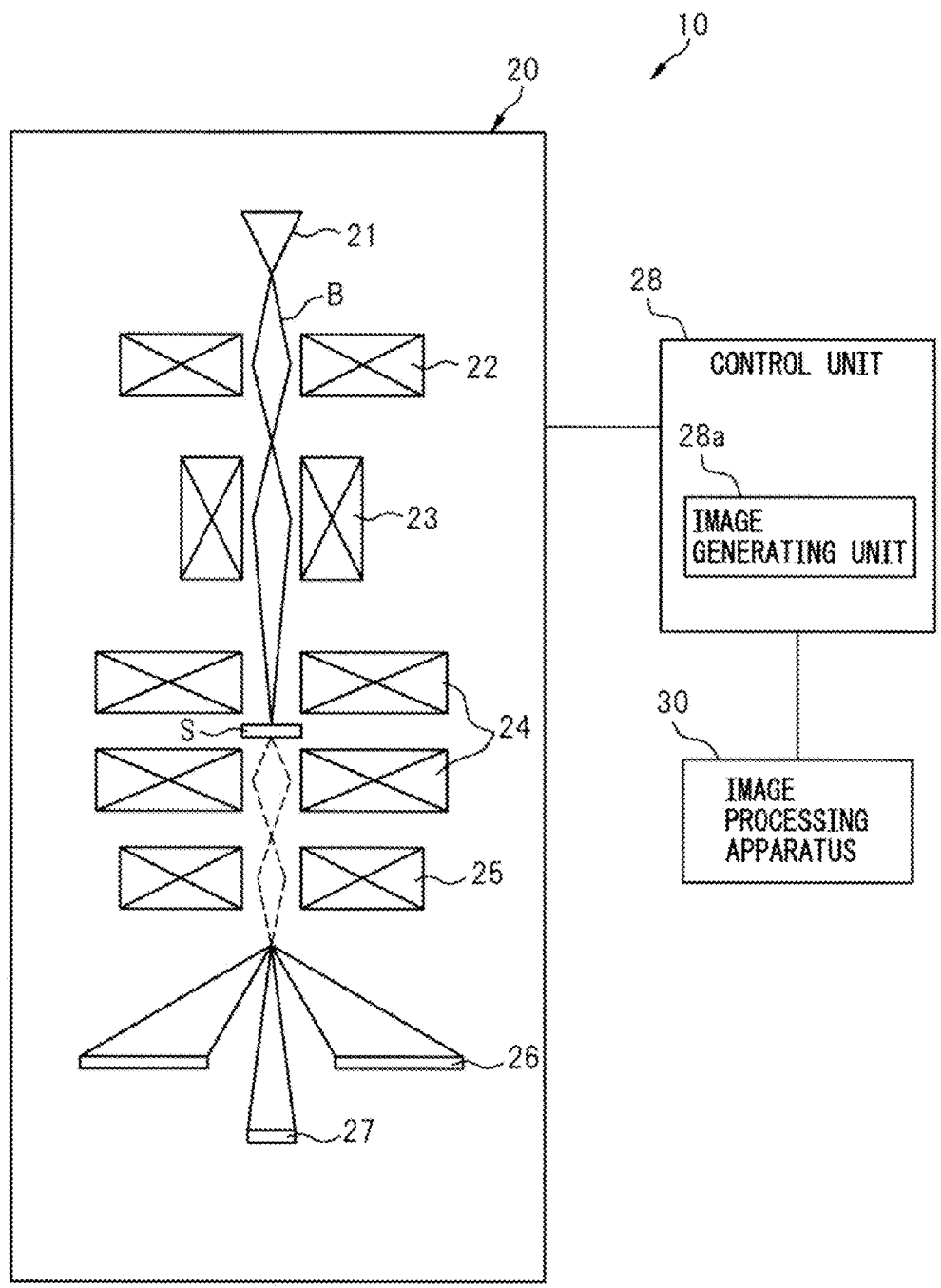
FIG. 3 is a diagram illustrating one embodiment of a system disclosed in this specification.
Figure 4:
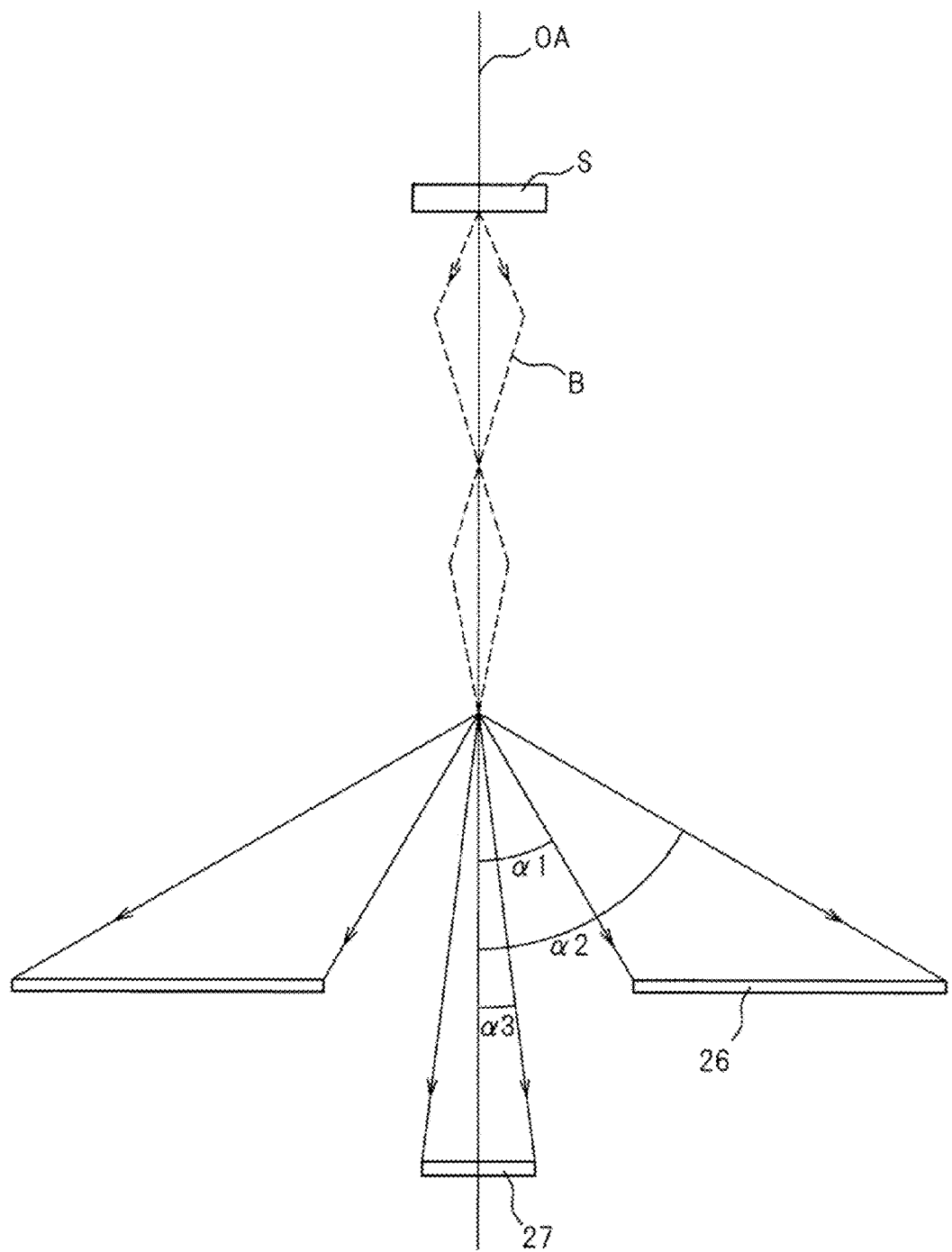
FIG. 4 is a diagram illustrating an essential portion of the system of FIG. 3.

FIG. 3 is a diagram illustrating one embodiment of the system disclosed in this specification. FIG. 4 is a diagram illustrating an essential portion of the system of FIG. 3.

The system 10 of this embodiment includes a scanning transmission electron microscope 20 and an image processing apparatus 30 which performs image processing by taking as inputs a dark-field image and a bright-field image produced by the scanning transmission electron microscope 20.

A sample S whose image is to be captured by the scanning transmission electron microscope 20 may have a periodic structure containing a plurality of atoms having different atomic numbers. Atoms with higher atomic numbers are atoms having relatively large and heavy mass, and may hereinafter be referred to simply as heavy atoms. On the other hand, atoms with lower atomic numbers are atoms having relatively small and light mass, and may hereinafter be referred to simply as light atoms.

The scanning transmission electron microscope 20 includes an electron source 21 which emits an electron beam B, a converging lens 22 which causes the electron beam B emitted from the electron source 21 to converge, and an objective lens 24 by which the electron beam B emitted from the electron source 21 is converged onto the sample S.

The scanning transmission electron microscope 20 further includes a scanning coil 23, disposed between the electron source 21 and the objective lens 24, for scanning the electron beam B across the surface of the sample S, and a focusing lens 25 by which the electron beam transmitted through the sample S is focused onto a back focal plane.

The scanning transmission electron microscope 20 further includes a first detector 26 for detecting electrons scattered at angles between a first angle $\alpha 1$ to the optical axis OA of the scanning transmission electron microscope and a second angle $\alpha 2$ which is larger than the first angle $\alpha 1$. The first detector 26 is an annular detector and is disposed in the back focal plane in which a dark-field image is formed. Hereinafter, the first detector 26 may also be referred to as the high-angle annular dark-field image detector. The optical axis OA of the scanning transmission electron microscope 20 coincides with the optical axes of the objective lens 24 and the focusing lens 25.

The scanning transmission electron microscope 20 further includes a second detector 27 for detecting electrons scattered within a third angle $\alpha 3$ which is smaller than the first angle $\alpha 1$. The second detector 27 is a circular detector and is disposed in the back focal plane in which a bright-field image is formed. Hereinafter, the second detector 27 may also be referred to as the low-angle bright-field image detector.

The scanning transmission electron microscope 20 further includes a control unit 28 which controls the electron source 21 or other components such as the lenses or coils described above. The control unit 28 includes an image generating unit 28a which generates a dark-field image based on a detection signal supplied from the first detector 26 and a bright-field image based on a detection signal supplied from the second detector 27. The image generating unit 28a supplies the thus generated dark-field image and bright-field image to the image processing apparatus 30.

The scanning transmission electron microscope 20 may also include a converging lens aperture for limiting unwanted spreading of the electron beam or a corrector for correcting for aberrations such as spherical or astigmatic aberrations.

The scanning transmission electron microscope 20 scans the surface of the sample S by using the convergent electron beam B, and acquires the dark-field image and the bright-field image simultaneously by obtaining the brightness of each pixel in the dark-field image and the bright-field image for each point scanned. Since the dark-field image and the bright-field image are both acquired in the same scanning operation, the number of pixels is the same between them.

The first angle $\alpha 1$ defines the lower limit of the electron scattering angle within which the scattered electrons can be detected by the high-angle annular dark-field image detector 26. The first angle $\alpha 1$ is an angle measured from the optical axis OA across the direction of travel of the electrons. The larger the first angle $\alpha 1$, the more preferable it is; preferably, the first angle $\alpha 1$ is set not smaller than 40 mrad. Usually, the first angle $\alpha 1$ is set to about 70 mrad.

The second angle $\alpha 2$ defines the upper limit of the electron scattering angle within which the scattered electrons can be detected by the high-angle annular dark-field image detector 26. The second angle $\alpha 2$ is an angle measured from the optical axis OA across the direction of travel of the electrons. The larger the second angle $\alpha 2$, the more preferable it is; preferably, the second angle $\alpha 2$ is set not smaller than 70 mrad. Usually, the second angle $\alpha 2$ is set to about 180 mrad.

It is preferable to set the third angle $\alpha 3$ based on the atomic number of the lighter atom among the heavy and light atoms composing the sample S. It is also preferable to set the upper limit of the third angle $\alpha 3$ so that the bright-field image captured using the low-angle bright-field image detector 27 does not resemble the complementary image of the dark-field image captured using the high-angle annular dark-field image detector 26, though the details will be described later.

For example, when the atomic number of the lighter atom is 8 or lower, it is preferable to set the third angle $\alpha 3$ within a range of 7 to 12 mrad.

If the third angle $\alpha 3$ is smaller than 7 mrad, the brightness of the atomic images may become unstable in the bright-field image captured using the low-angle bright-field image detector 27. On the other hand, if the third angle $\alpha 3$ is larger than 12 mrad, the bright-field image captured using the low-angle bright-field image detector 27 begins to resemble the complementary image of the dark-field image captured using the high-angle annular dark-field image detector 26, which is not desirable.

Next, the image processing apparatus 30 will be described below with reference to drawings.

Figure 5:
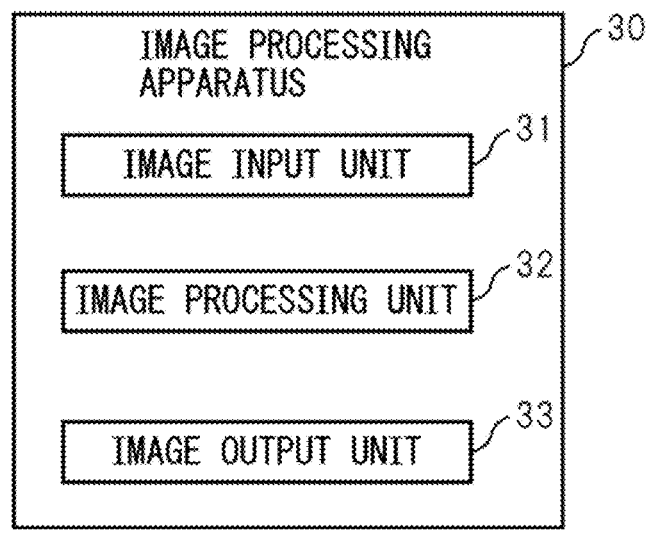
FIG. 5 is a block diagram of an image processing apparatus.
Figure 6:
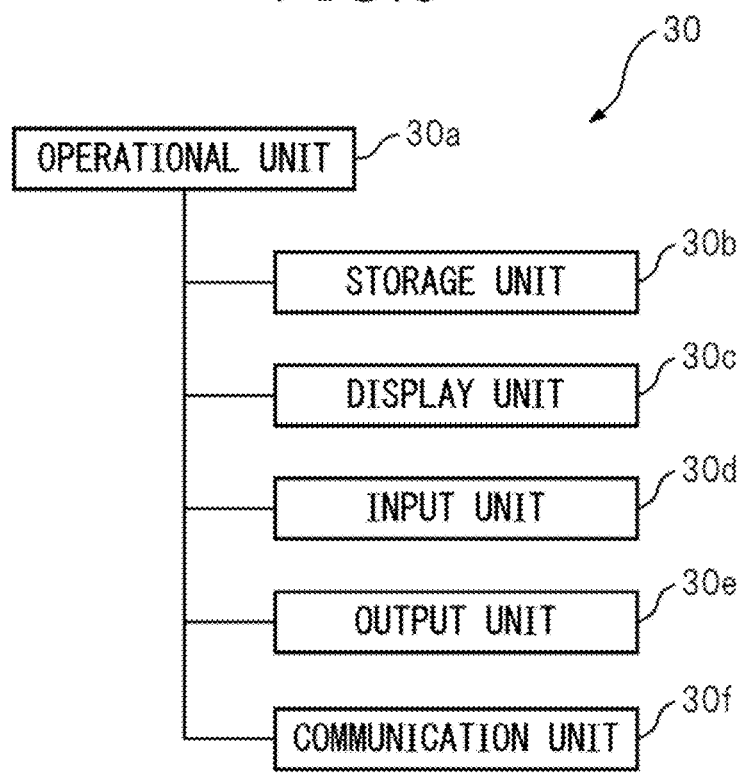
FIG. 6 is a diagram illustrating the hardware configuration of the image processing apparatus.

FIG. 5 is a block diagram of the image processing apparatus. FIG. 6 is a diagram illustrating the hardware configuration of the image processing apparatus.

As depicted in FIG. 5, the image processing apparatus 30 includes an image input unit 31 which takes as inputs the dark-field image and bright-field image generated by the image generating unit 28a, an image processing unit 32 which generates a reverse image by reversing the lightness and darkness of the dark-field image, and generates a difference image each of whose pixels has a brightness value equal to the difference between the brightness of the corresponding pixel in the reverse image and the brightness of the corresponding pixel in the bright-field image, and an image output unit 33 which outputs the thus generated difference image.

As depicted in FIG. 6, the image processing apparatus 30 includes, as the hardware for implementing the above functions, an operational unit 30a, a storage unit 30b, a display unit 30c, an input unit 30d, an output unit 30e, and a communication unit 30f. The operational unit 30a implements each function of the image processing apparatus 30 by executing a prescribed program stored in the storage unit 30b.

The prescribed program may be loaded into the storage unit 30b via a network (not depicted) by using, for example, the communication unit 30f. Further, the dark-field image and the bright-field image may be loaded via a network by connecting the communication unit 30f of the image processing apparatus 30 to the control unit 28 of the scanning transmission electron microscope 20 via the network.

The image processing apparatus 30 can be constructed using, for example, a server or a computer such as a personal computer, or a state machine or the like. The control unit 28 of the scanning transmission electron microscope 20 can be implemented using hardware similar to that depicted in FIG. 6.

Of the heavy atoms and light atoms composing the sample S, the atomic images of the heavy atoms appear as high-brightness images (for example, bright spots) in the dark-field image produced by the scanning transmission electron microscope 20. However, the light atoms are usually difficult to visually recognize because of their low brightness.

On the other hand, of the heavy atoms and light atoms composing the sample S, the atomic images of the heavy atoms appear as low-brightness images (for example, dark spots) in the bright-field image produced by the scanning transmission electron microscope 20, and the light atoms appear as higher brightness images (for example, brighter spots) than the heavy atoms. Accordingly, in the bright-field image produced by the scanning transmission electron microscope 20, the atomic images of the heavy atoms appear black, and the atomic images of the light atoms appear white. In this way, while the bright-field image produced by the scanning transmission electron microscope 20 displays both the heavy atoms and the light atoms, either the heavy atoms or the light atoms are displayed as bright spots and the other as dark spots. There are therefore cases where it is difficult to accurately observe the arrangement of the respective atoms because of the influence of background brightness, etc. If the sample contains three or more kinds of atoms having different atomic numbers, it is even more difficult to accurately observe the arrangement of the atoms.

The image processing apparatus 30 performs image processing using the bright-field image and the dark-field image so that the heavy atoms and light atoms composing the sample S are both displayed as dark spots, though there is a finite difference in brightness, and thereby generates an image that enables the viewer to accurately observe the arrangement of the atoms. By using such an electron micrograph image, both the heavy atoms and light atoms can be observed simultaneously.

Next, the method of image processing that the image processing apparatus 30 performs will be described in the following order.

(1) First, a description will be given of the concept of image processing for generating an electron micrograph image on which both the heavy atoms and light atoms can be observed simultaneously.

(2) Next, to verify the above concept, an electron micrograph image on which both the heavy atoms and light atoms can be observed simultaneously is generated using electron micrograph images obtained by calculation.

(3) Finally, a description will be given of the normalizations to be performed when performing image processing on the bright-field image and dark-field image produced by the scanning transmission electron microscope.

(1) Description of the concept of image processing for generating an electron micrograph image on which both the heavy atoms and light atoms can be observed simultaneously FIGS. 7 to 10 are diagrams illustrating the concept of image processing for generating an electron micrograph image on which both the heavy atoms and light atoms can be observed simultaneously.

Figure 1:
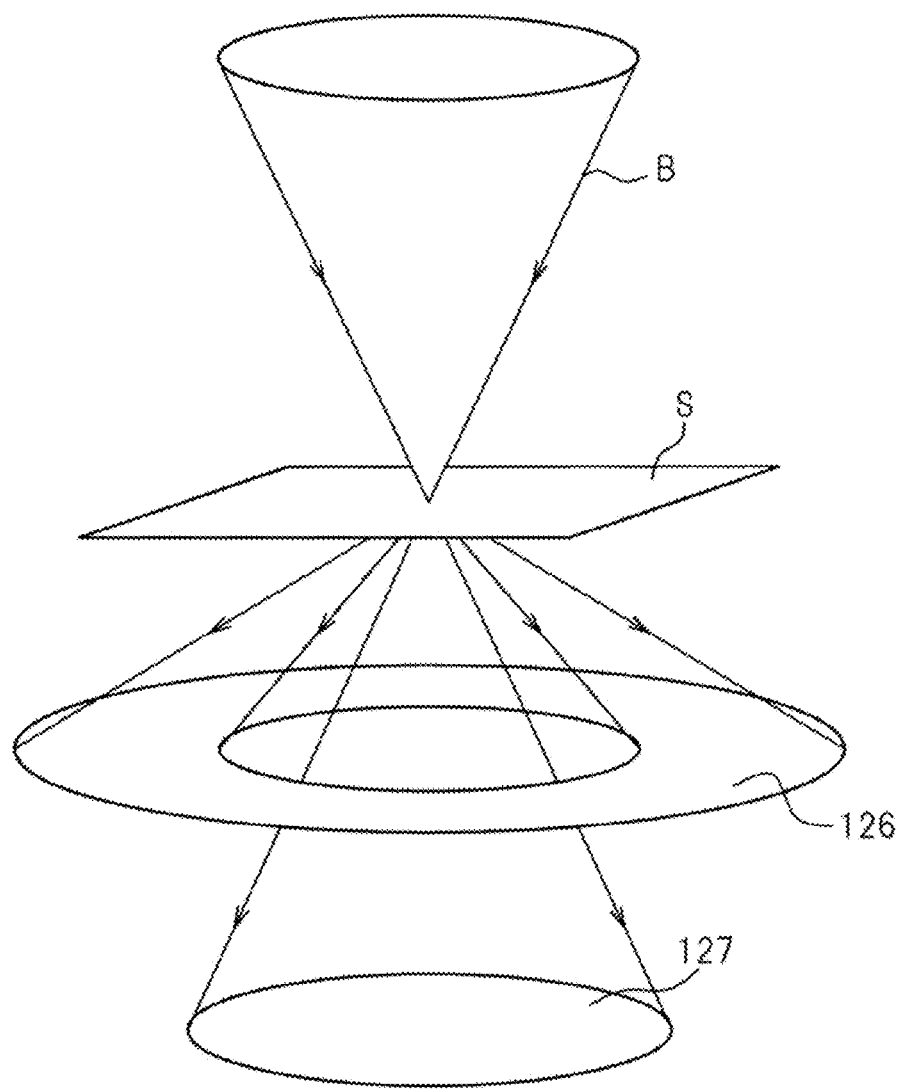
FIG. 1 is a diagram schematically illustrating a scanning transmission electron microscope according to a prior art example.
Figure 2:
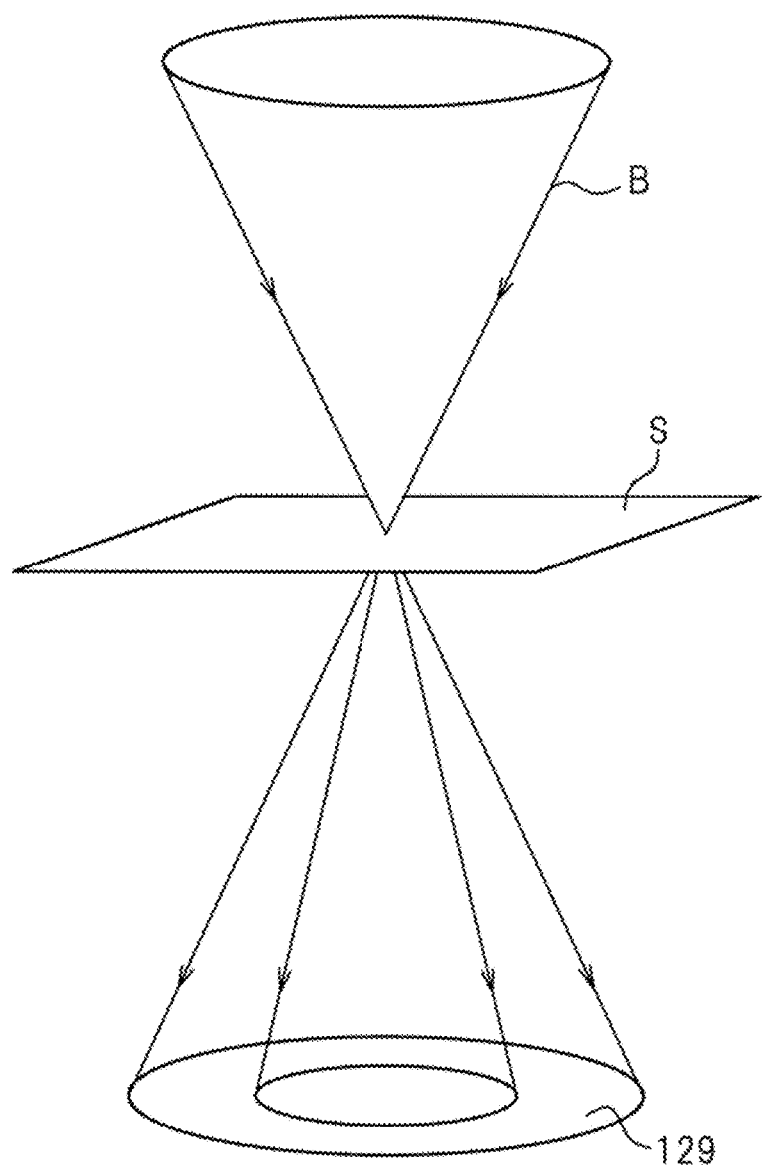
FIG. 2 is a diagram schematically illustrating a scanning transmission electron microscope according to another prior art example.

Based on the dark-field image captured using the high-angle annular dark-field image detector 26 and the bright-field image captured simultaneously with the dark-field image by using the low-angle bright-field image detector 27, the image processing apparatus 30 generates an electron micrograph image corresponding to the bright-field image captured using the annular detector depicted in FIG. 2.

Figure 7:
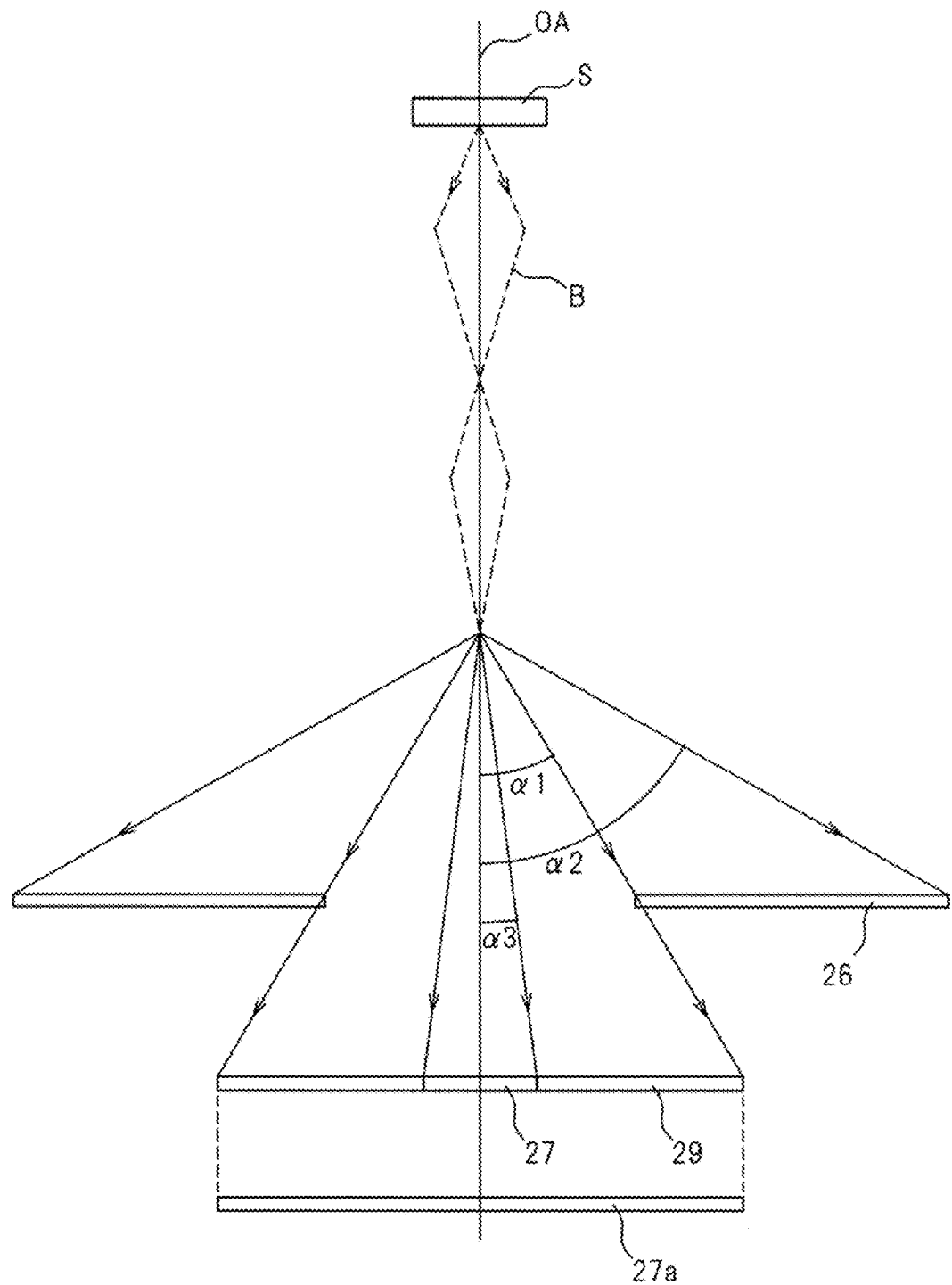
FIG. 7 is a diagram (part 1) illustrating the concept of image processing for generating an electron micrograph image on which both heavy atoms and light atoms can be observed simultaneously.

FIG. 7 illustrates the condition in which the annular detector 29 depicted in FIG. 2 is added in a virtual manner in the scanning transmission electron microscope depicted in FIG. 4. The annular detector 29 detects electrons transmitted through the sample S and scattered at angles between the third angle α3 and the first angle α1 as measured relative to the optical axis OA. Hereinafter, the annular detector 29 may also be referred to as the high-angle annular bright-field image detector.

In FIG. 7 there is also depicted a circular detector 27a constructed by combining the high-angle annular bright-field image detector 29 with the low-angle bright-field image detector 27 in an integral fashion. Hereinafter, the circular detector 27a may also be referred to as the high-angle bright-field image detector. The high-angle bright-field image detector 27a detects electrons scattered at angles smaller than the first angle α1 relative to the optical axis OA.

Figure 8:
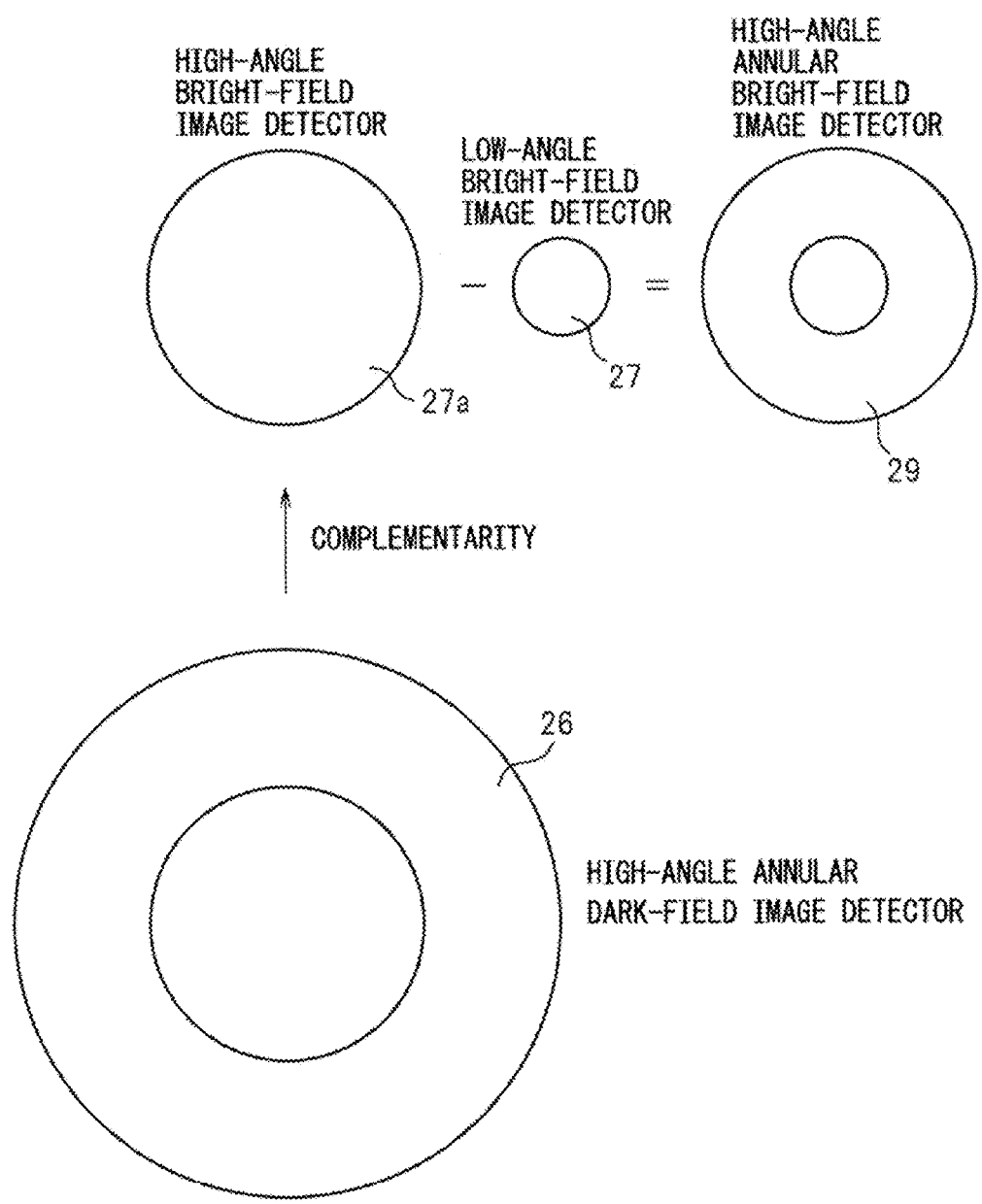
FIG. 8 is a diagram (part 2) illustrating the concept of image processing for generating an electron micrograph image on which both heavy atoms and light atoms can be observed simultaneously.

As illustrated in FIG. 8, the high-angle annular bright-field image detector 29 corresponds to the high-angle bright-field image detector 27a from which the portion corresponding to the low-angle bright-field image detector 27 has been removed.

The applicant has discovered, as illustrated in FIG. 9, that the bright-field image captured using the high-angle annular bright-field image detector 29 is a difference image each of whose pixels has a brightness value equal to the difference between the brightness of the corresponding pixel in the bright-field image captured using the high-angle bright-field image detector 27a and the brightness of the corresponding pixel in the bright-field image captured using the low-angle bright-field image detector 27.

Next, referring to FIG. 10, a description will be given of how the difference image representing the difference between the bright-field image captured using the high-angle bright-field image detector 27a and the bright-field image captured using the low-angle bright-field image detector 27 provide atomic images in which the heavy atoms and light atoms composing the sample S are both displayed as dark spots.

FIG. 10(A) depicts the structure of an atomic arrangement in which the heavy atoms H and light atoms L composing the sample S are arranged alternately.

FIG. 10(B) depicts the electron beam intensity profile taken along the arrowed line in FIG. 10(A) in the bright-field image of the sample S captured using the high-angle bright-field image detector 27a. In FIG. 10(B), the abscissa represents the scanned position along the atomic arrangement, and the ordinate represents the electron beam intensity detected by the detector.

In FIG. 10(B), a peak P1 having an intensity lower than the baseline appears at a position corresponding to each heavy atom H. Since the heavy atom H has strong thermal diffuse scattering, many electrons are scattered at scattering angles not smaller than the first angle α1; as a result, in the bright-field image generated based on the electrons scattered at scattering angles smaller than the first angle α1, the atomic image of the heavy atom H is displayed as a dark spot. On the other hand, no peaks indicating the presence of atoms appear at positions corresponding to the light atoms L.

FIG. 10(C) depicts the electron beam intensity profile taken along the arrowed line in FIG. 10(A) in the bright-field image of the sample S captured using the low-angle bright-field image detector 27. In FIG. 10(C), the abscissa represents the scanned position along the atomic arrangement, and the ordinate represents the electron beam intensity detected by the detector.

In FIG. 10(C), a peak P2 having an intensity higher than the baseline appears at a position corresponding to each light atom L. Further, in FIG. 10(C), a peak P3 having an intensity lower than the baseline appears at a position corresponding to each heavy atom H. Since the size of the low-angle bright-field image detector 27 is smaller than the size of the high-angle bright-field image detector 27a, the peak P3 is smaller than the peak P1.

In FIG. 10(D), the difference between the electron beam intensity depicted in FIG. 10(B) and the electron beam intensity depicted in FIG. 10(C), taken along the arrowed line in FIG. 10(A), is displayed.

In FIG. 10(D), a peak P4 having an intensity lower than the baseline appears at a position corresponding to each heavy atom H, and a peak P5 having an intensity lower than the baseline appears at a position corresponding to each light atom L. The peaks P4 and P5, whose intensities are lower than the baseline, are both displayed as dark spots in the resulting image.

In this way, the images of the heavy atoms H and light atoms L composing the sample S are both displayed as dark spots in the difference image.

The applicant already reported that the dark-field image captured using the high-angle annular dark-field image detector 26 corresponds to the complementary image of the bright-field image captured using the high-angle bright-field image detector 27a (refer to Acta Crystallographica Section A: Foundations of Crystallography 60 (2004)591, by K. Watanabe, et al.).

That is, as illustrated in FIG. 9, the reverse image generated by reversing the lightness and darkness of the dark-field image captured using the high-angle annular dark-field image detector 26 corresponds to the bright-field image captured using the high-angle bright-field image detector 27a.

Then, by taking advantage of the above complementarity, the high-angle annular dark-field image detector 26 is used in place of the high-angle bright-field image detector 27a, as illustrated in FIG. 8.

More specifically, the system 10 generates a difference image each of whose pixels has a brightness value equal to the difference between the brightness of the corresponding pixel in the reverse image generated by reversing the lightness and darkness of the dark-field image captured using the high-angle annular dark-field image detector 26 and the brightness of the corresponding pixel in the bright-field image captured using the low-angle bright-field image detector 27. As illustrated in FIG. 9, this difference image corresponds to the bright-field image that would be captured using the high-angle annular bright-field image detector 29.

Since the dark-field image captured using the high-angle annular dark-field image detector 26 and the bright-field image captured using the low-angle bright-field image detector 27 are both acquired in the same scanning operation, the number of pixels is the same between them, and therefore, the difference image can be obtained by calculating the differences between the brightness values of the respectively corresponding pixels.

The high-angle annular dark-field image detector 26 and the low-angle bright-field image detector 27 are standard detectors used in the conventional scanning transmission electron microscope. In this way, in the system 10, an image corresponding to the bright-field image that would be captured using the high-angle annular bright-field image detector 29 is generated using the high-angle annular dark-field image detector 26 and the low-angle bright-field image detector 27, without using any additional detector such as the high-angle annular dark-field image detector 26.

To display the atomic images of the heavy atoms and light atoms with good contrast in the difference image, it is desirable that a good contrast dark-field image be generated using the high-angle annular dark-field image detector 26. It is therefore desirable that the dark-field image captured using the high-angle annular dark-field image detector 26 be one that is captured with a defocus value that maximizes the contrast. Usually, the focus position that maximizes the contrast is near the exact focal point, but since it does not necessarily follow that the maximum contrast can be obtained at the position corresponding to the positive focal point, it is preferable to capture the dark-field image at an out-of-focus position where the maximum contrast can be obtained. The term out-of-focus position used here is meant to also include the position corresponding to the exact focal point.

As the third angle $\alpha 3$ nears the first angle $\alpha 1$, the size of the low-angle bright-field image detector 27 nears that of the high-angle bright-field image detector 27a (see FIG. 7). Accordingly, as the third angle $\alpha 3$ nears the first angle $\alpha 1$, the bright-field image captured using the low-angle bright-field image detector 27 comes to resemble the bright-field image captured using the high-angle bright-field image detector 27a. It is therefore preferable to set the third angle $\alpha 3$ so that the bright-field image captured using the low-angle bright-field image detector 27 does not resemble the bright-field image captured using the high-angle bright-field image detector 27a. That is, it is preferable to set the third angle $\alpha 3$ so that the bright-field image captured using the low-angle bright-field image detector 27 does not resemble the complementary image of the dark-field image captured using the high-angle annular dark-field image detector 26.

(2) Description of how an electron micrograph image on which both the heavy atoms and light atoms can be observed simultaneously is generated using electron micrograph images obtained by calculation Next, to actually verify the concept of the different image generation described above, the bright-field image captured using the high-angle bright-field image detector 27a and the bright-field image captured using the low-angle bright-field image detector 27 were each obtained by calculation, and their difference image was generated.

Figure 11:
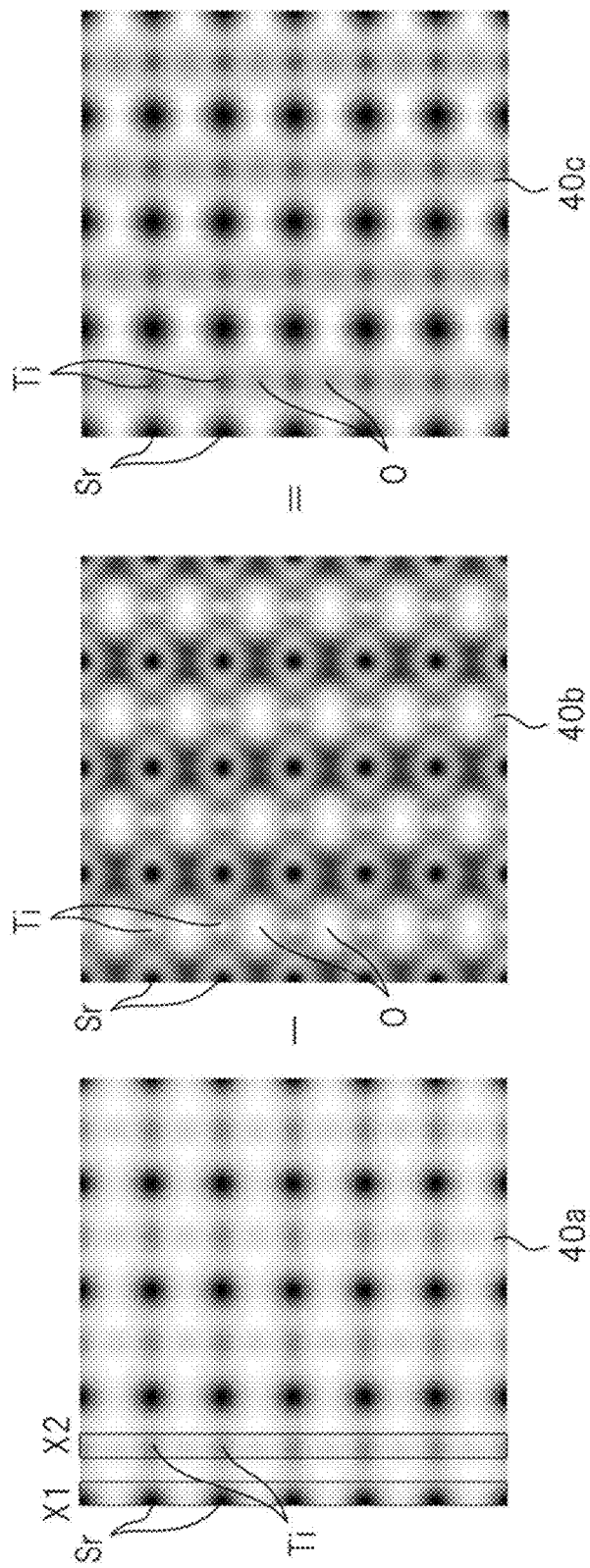
FIG. 11 is a diagram (part 1) illustrating the generation of a difference image by calculation.
Figure 12:
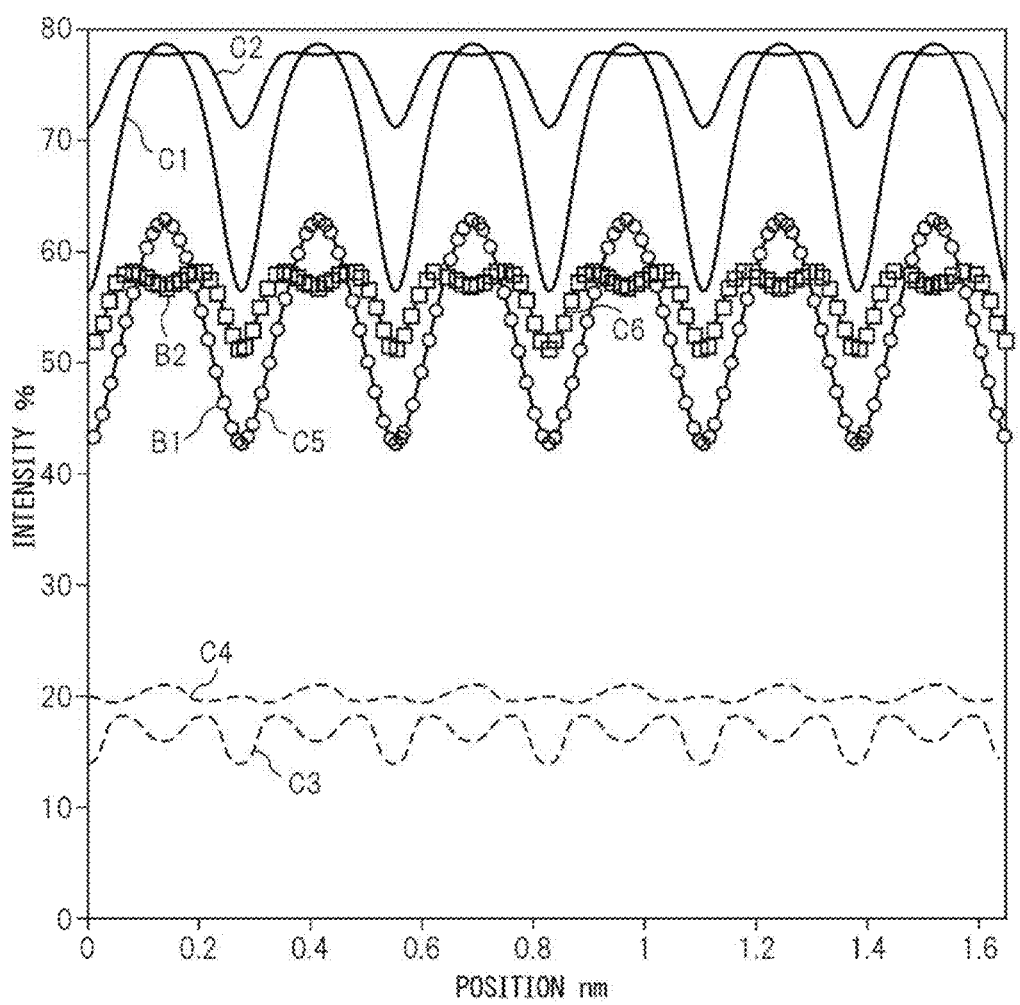
FIG. 12 is a diagram (part 2) illustrating the generation of a difference image by calculation.

FIGS. 11 and 12 are diagrams illustrating the generation of the difference image by calculation.

In FIG. 11, an image 40a represents an image obtained by calculating the bright-field image of the (011) plane of $SrTiO_3$, the sample under inspection, captured using the high-angle bright-field image detector 27a depicted in FIG. 7. On the other hand, an image 40b, which corresponds to the image 40a, represents an image obtained by calculating the bright-field image of the (011) plane of $SrTiO_3$ captured using the low-angle bright-field image detector 27 depicted in FIG. 7. Further, an image 40c, which also corresponds to the image 40a, represents an image obtained by calculating the bright-field image of the (011) plane of $SrTiO_3$ captured using the high-angle annular bright-field image detector 29 depicted in FIG. 7.

When the sample is $SrTiO_3$, the Sr and Ti atoms correspond to the heavy atoms, and the O atoms correspond to the light atoms.

The Bethe method (i.e., the Bloch wave method) or the multi-slice method can be used for the calculation of the above bright-field images. The calculation conditions were set as follows: the acceleration voltage was 200 kV, the convergence angle of the electron beam was 20 mrad, the spherical aberration coefficient was −0.5 μm, and the chromatic aberration coefficient was 1.7 mm. The thickness of the sample was 30 nm.

In the image 40a of FIG. 11, the atomic image of each Sr atom is displayed as a dark spot. Further, in the image 40a, the atomic image of each Ti atom is also displayed as a dark spot, though it is brighter than the Sr atomic image. However, in the image 40a, the O atoms are not recognizable.

In the image 40b of FIG. 11, the atomic image of each Sr atom is displayed as a dark spot. In the image 40b, the atomic image of each Ti atom is displayed as a bright spot. Further, in the image 40b, the atomic image of each O atom is also displayed as a bright spot.

In the image 40c of FIG. 11, the atomic image of each Sr atom is displayed as a dark spot. Further, in the image 40c, the atomic image of each Ti atom is also displayed as a dark spot, though it is brighter than the Sr atomic image. Furthermore, in the image 40c, the atomic image of each O atom is also displayed as a dark spot, though it is brighter than the Ti atomic image.

FIG. 12 displays the intensities of the electrons detected along lines X1 and X2 in the image 40a of FIG. 11. Curve C1 represents the detected electron intensity taken along the line X1, while curve C2 represents the detected electron intensity taken along the line X2. The detected electron intensity plotted along the ordinate in FIG. 12 is defined as the percentage of the amount of electrons detected by the detector relative to the total amount of electrons incident on the sample. The detected electron intensity plotted along the ordinate in FIG. 12 corresponds to the pixel brightness value in each of the images 40a, 40b, and 40c.

FIG. 12 further displays the intensities of the electrons detected at the positions on the image 40b of FIG. 11 that correspond the lines X1 and X2 in the image 40a. Curve C3 represents the detected electron intensity taken along the line X1, while curve C4 represents the detected electron intensity taken along the line X2.

FIG. 12 further displays the intensities of the electrons detected at the positions on the image 40c of FIG. 11 that correspond to the lines X1 and X2 in the image 40a of FIG. 11. Curve C5 represents the detected electron intensity taken along the line X1, while curve C6 represents the detected electron intensity taken along the line X2.

In FIG. 12, there is also displayed a plot B1 constructed by plotting the difference between the curve C1 and the curve C3. The plot B1 coincides with the curve C5.

Likewise, in FIG. 12, there is also displayed a plot B2 constructed by plotting the difference between the curve C2 and the curve C4. The plot B2 coincides with the curve C6.

Thus, it has been verified that the difference image representing the difference between the bright-field image captured using the high-angle bright-field image detector 27a and the bright-field image captured using the low-angle bright-field image detector 27 coincides with the bright-field image captured using the high-angle annular bright-field image detector 29.

(3) Description of the normalizations to be performed when performing image processing on the bright-field image and dark-field image produced by the scanning transmission electron microscope To obtain the above difference image, the difference between the electron intensity as the brightness of the bright-field image captured using the high-angle bright-field image detector 27a and the electron intensity as the brightness of the corresponding pixel in the bright-field image captured using the low-angle bright-field image detector 27 is directly calculated.

However, in the actually produced electron micrograph image, since the detection sensitivity of the high-angle annular dark-field image detector 26 and the detection sensitivity of the low-angle bright-field image detector 27 differ from each other, there is a need, before obtaining the difference, to normalize the brightness for both the bright-field image and the reverse image generated by reversing the lightness and darkness of the dark-field image. Therefore, in the system 10, the brightness is normalized in the following manner.

First, a calculated reverse image, which is a calculated scanning transmission electron micrograph image corresponding to the reverse image, and a calculated bright-field image, which is a calculated scanning transmission electron micrograph image corresponding to the bright-field image, are obtained using the crystal structure of the sample S determined based on the atomic images detected on the captured dark-field image.

When the sample S whose image is to be captured contains both heavy atoms and light atoms, the atomic images of the heavy atoms appear in the dark-field image captured using the high-angle annular dark-field image detector 26, but the atomic images of the light atoms may not appear in the dark-field image. Usually, the sample S is an unknown material. Then, from the captured dark-field image, the fact that the sample S at least contains heavy atoms is obtained as the information concerning the sample S of unknown material, together with the arrangement of the atomic images of the heavy atoms.

The crystal structure of the sample S is then determined based on the atomic images detected on the captured dark-field image. It is preferable to determine the crystal structure of the sample S by also using other analysis results obtained by measuring the same sample S using such techniques as X-ray diffraction analysis. If it can be seen from the captured dark-field image that the crystal structure of the sample S contains defects, the crystal structure containing such defects may be obtained.

The calculated reverse image and the calculated bright-field image can be obtained using the earlier noted Bethe method (i.e., the Bloch wave method) or the multi-slice method. Further, as the calculation conditions for the calculated reverse image and the calculated bright-field image, it is preferable to use the same conditions as those used by the scanning transmission electron microscope to capture the dark-field and bright-field images.

If the sample S is a known material, the crystal structure of the known sample S may be used.

Next, the reverse image is normalized so that the maximum and minimum values of brightness in the reverse image agree with the maximum and minimum values of brightness in the calculated reverse image. At the same time, the bright-field image is normalized so that the maximum and minimum values of brightness in the bright-field image agree with the maximum and minimum values of brightness in the calculated bright-field image.

When generating the reverse image by reversing the lightness and darkness of the dark-field image, if the brightness of each pixel in the dark-field image is represented by an 8-bit value in the range of 0 to 255, for example, the reverse image may be generated by multiplying the brightness value of each pixel by −1 so that the brightness of each pixel in the reverse image is represented by a value in the range of −255 to 0. Alternatively, the reverse image may be generated by subtracting the brightness value of each pixel in the dark-field image from 255 so that the brightness of each pixel in the reverse image is represented by a value in the range of 0 to 255.

The reverse image may be normalized, for example, by performing the following procedure. First, the maximum value BMa and the minimum value BMi of brightness are obtained from the reverse image. Next, the maximum value CMa and the minimum value CMi of brightness are obtained from the calculated reverse image. Then, by solving the simultaneous equations $CMa=A \cdot BMa+B$ and $CMi=A \cdot BMi+B$, the unknowns A and B are found. Then, using the thus found A and B, the brightness of each pixel in the reverse image is normalized.

The bright-field image can be normalized in a similar manner.

Next, to actually verify the normalization concept described above, normalizations were performed using the bright-field image and dark-field image obtained by calculation.

Figure 13:
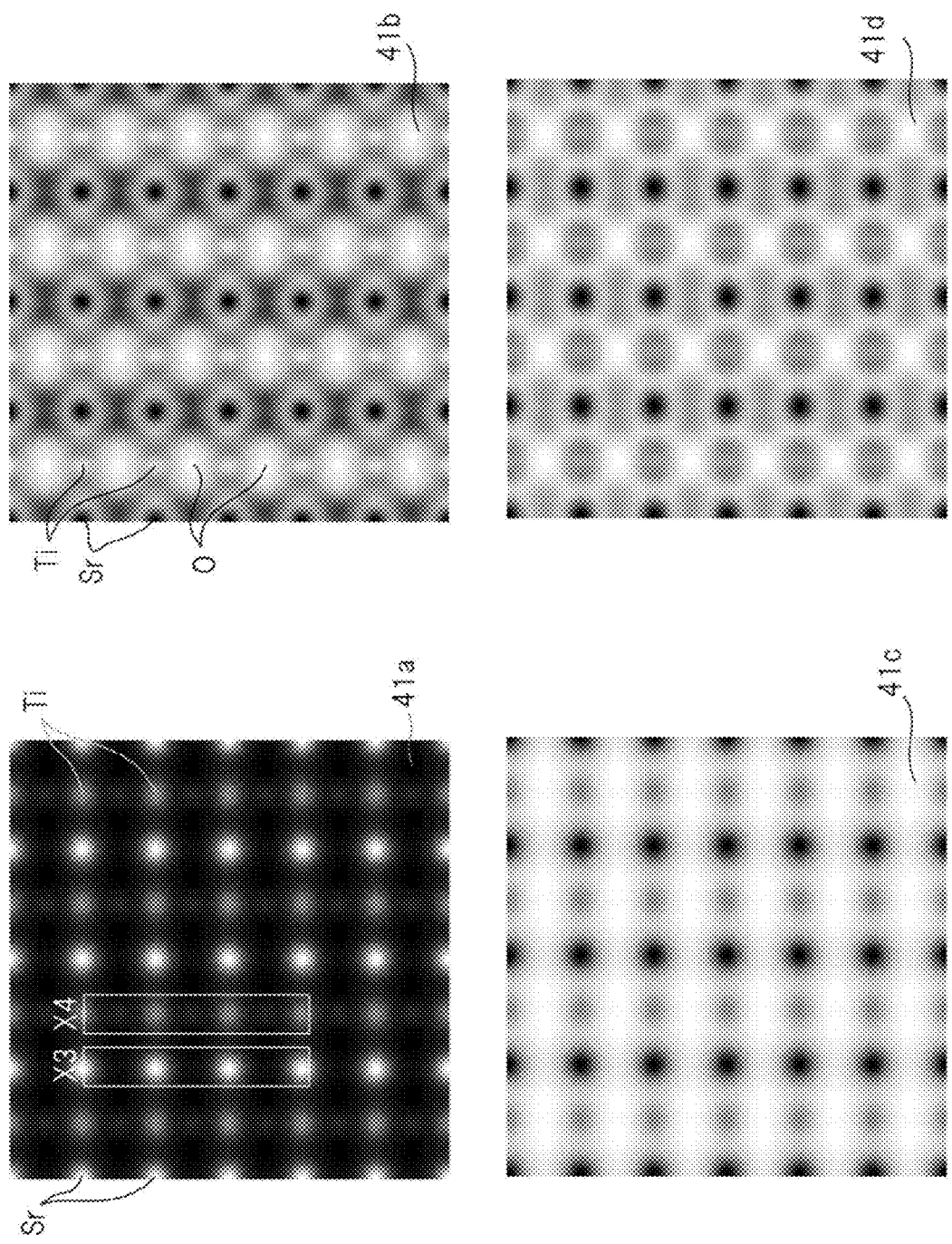
FIG. 13 is a diagram (part 1) illustrating bright-field and dark-field image normalizations.
Figure 14:
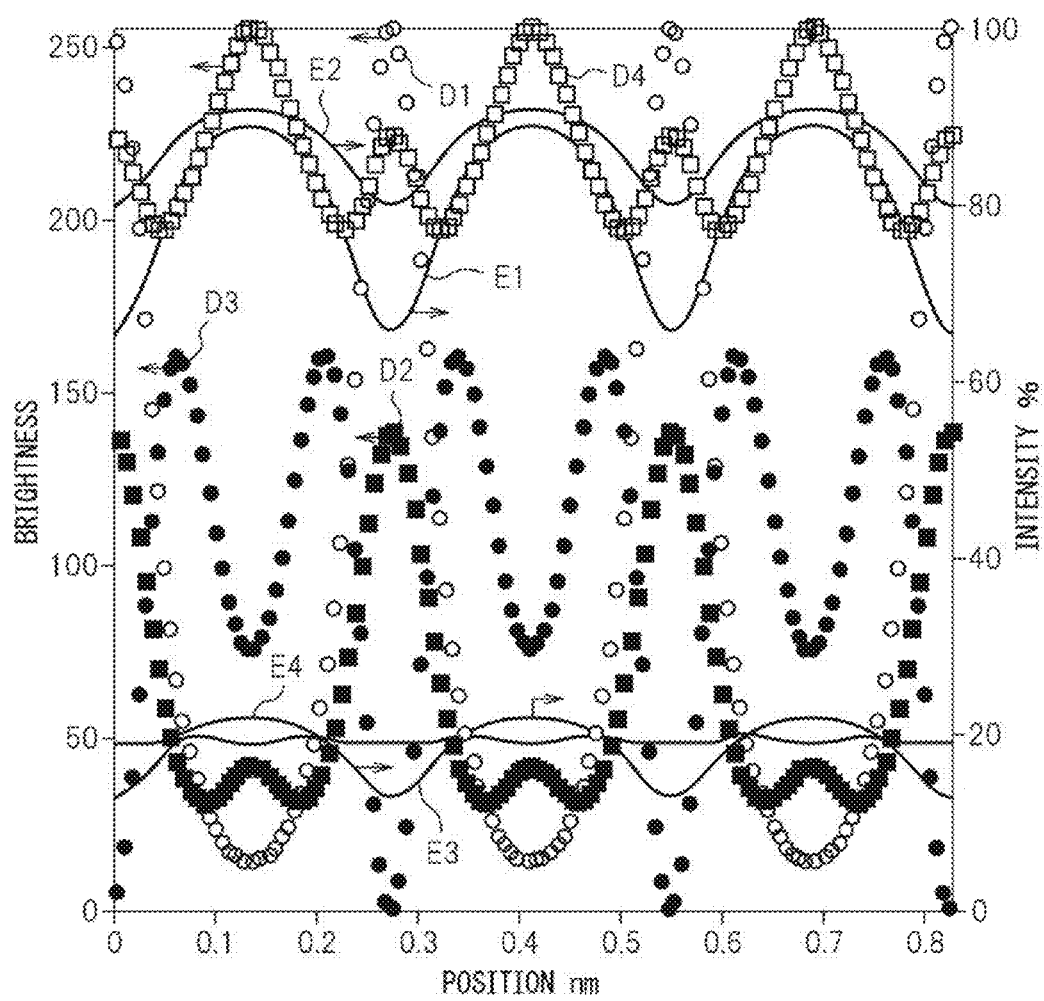
FIG. 14 is a diagram (part 2) illustrating bright-field and dark-field image normalizations.
Figure 15:
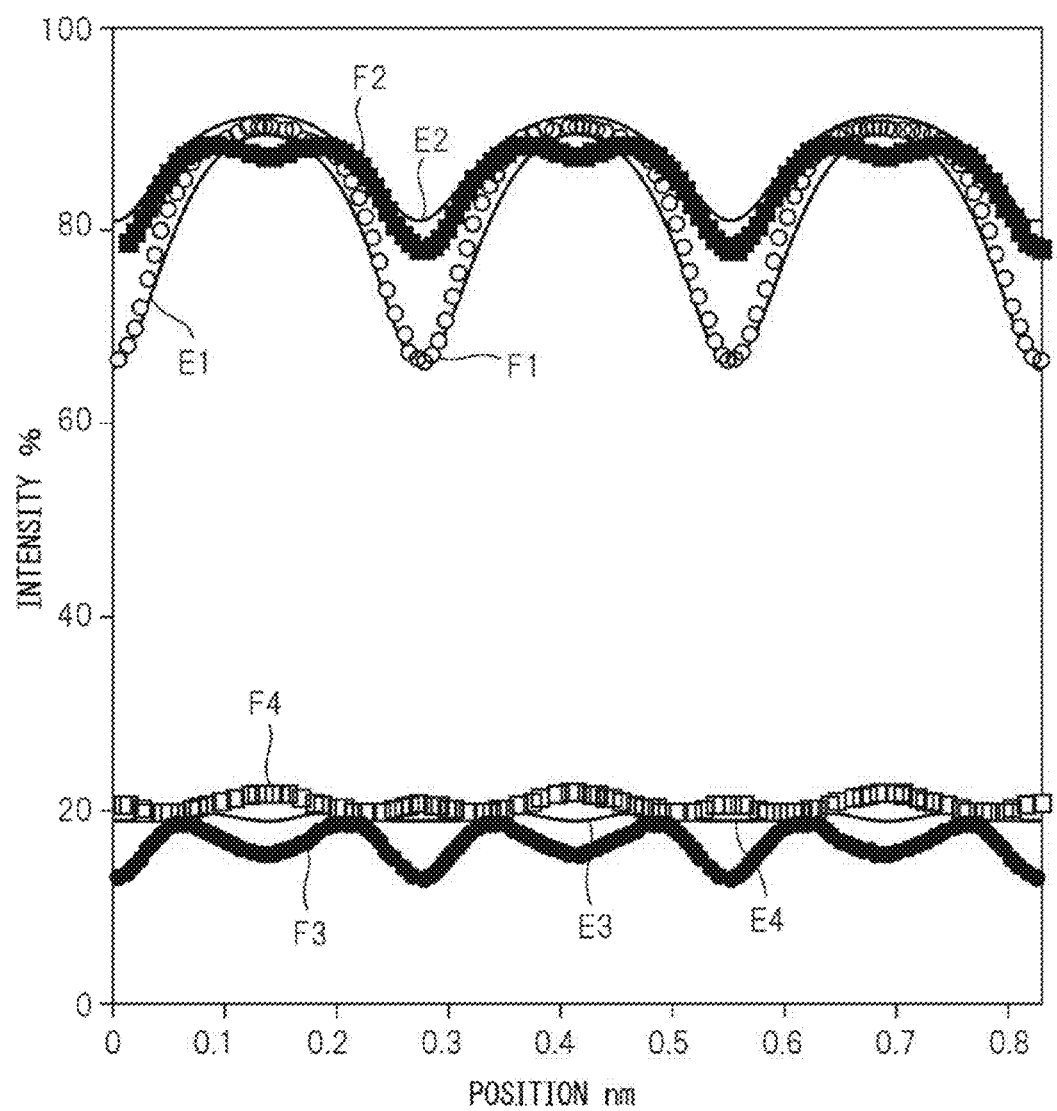
FIG. 15 is a diagram (part 3) illustrating bright-field and dark-field image normalizations.

FIGS. 13 to 15 are diagrams illustrating the normalizations for the bright-field image and dark-field image.

In FIG. 13, an image 41a represents an image obtained by calculating the dark-field image of the (011) plane of $SrTiO_3$ captured using the high-angle annular dark-field image detector 26 depicted in FIGS. 3 and 4. On the other hand, an image 41*b*, which corresponds to the image 41*a*, represents an image obtained by calculating the bright-field image of the (011) plane of SrTiO$_3$ captured using the low-angle bright-field image detector 27 depicted in FIGS. 3 and 4.

In the image 41*a* of FIG. 13, the atomic image of each Sr atom is displayed as a bright spot. Further, in the image 41*a*, the atomic image of each Ti atom is also displayed as a bright spot, though it is darker than the Sr atomic image. However, in the image 41*a*, the O atoms are not recognizable. The image 41*a* in FIG. 13 corresponds to a reverse image obtained by reversing the lightness and darkness of the image 40*a* depicted in FIG. 11.

The image 41*b* in FIG. 13 is the same as the image 40*b* depicted in FIG. 11.

The image 41*c* in FIG. 13 represents a calculated reverse image which is a scanning transmission electron micrograph image corresponding to the reverse image of the image 41*a* and calculated using the crystal structure of the sample determined based on the atomic images detected on the dark-field image 41*a*. On the other hand, the image 41*d* represents a calculated bright-field image which is a scanning transmission electron micrograph image corresponding to the bright-field image 41*b* and calculated using the crystal structure of the sample determined based on the atomic images detected on the dark-field image 41*a*. Since the crystal structure of the sample was known, the crystal structure of SrTiO$_3$ from which the O atoms had been removed was used as the crystal structure of the sample determined based on the atomic images detected on the dark-field image 41*a*.

The calculation conditions were set as follows: the acceleration voltage was 200 kV, the convergence angle of the electron beam was 20 mrad, the spherical aberration coefficient was −0.5 μm, and the chromatic aberration coefficient was 1.7 mm. The thickness of the sample was 30 nm. These conditions are the same as those used in FIGS. 11 and 12. The calculations were performed by using a different value for the detection sensitivity of the high-angle annular dark-field image detector 26 than for the detection sensitivity of the low-angle bright-field image detector 27.

FIG. 14 displays the intensities of the electrons detected along lines X3 and X4 in the image 41*a* of FIG. 13. Plot D1 represents the detected electron intensity taken along the line X3, while plot D2 represents the detected electron intensity taken along the line X4.

Further, FIG. 14 displays the intensities of the electrons detected at the positions on the image 41*b* of FIG. 13 that correspond the lines X3 and X4 in the image 41*a*. Plot D3 represents the detected electron intensity taken along the line X3, while plot D4 represents the detected electron intensity taken along the line X4.

The detected electron intensities of the plots D1 to D4 are represented by the values of 0 to 255 (along the ordinate at the left in FIG. 14) indicating the brightness of the respective images in FIG. 13.

FIG. 14 also displays the intensities of the electrons detected at the positions on the image 41*c* of FIG. 13 that correspond the lines X3 and X4 in the image 41*a*. Line E1 represents the detected electron intensity taken along the line X3, while line E2 represents the detected electron intensity taken along the line X4.

FIG. 14 further displays the intensities of the electrons detected at the positions on the image 41*d* of FIG. 13 that correspond the lines X3 and X4 in the image 41*a*. Line E3 represents the detected electron intensity taken along the line X3, while line E4 represents the detected electron intensity taken along the line X4.

The detected electron intensity plotted along each of the lines E1 to E4 is defined as the percentage of the amount of electrons detected by the detector relative to the total amount of electrons incident on the sample.

In FIG. 15, a plot F1 is depicted which represents the detected electron intensity taken along the line X3 in the reverse image obtained by normalizing the reverse image generated by reversing the lightness and darkness of the image 41*a*. In FIG. 15, a plot F2 is also depicted which represents the detected electron intensity taken along the line X4 in the reverse image obtained by normalizing the reverse image generated by reversing the lightness and darkness of the image 41*a*. The values of the plots F1 and F2 are each given as the percentage of the amount of electrons detected by the detector relative to the total amount of electrons incident on the sample.

The plot F1 agrees well with the line E1. On the other hand, the plot F2 agrees well with the line E2, though there are finite differences due to the presence or absence of O atoms.

In FIG. 15, there is also depicted a plot F3 which represents the detected electron intensity taken along the line X3 in the image obtained by normalizing the image 41*c*. FIG. 15 further depicts a plot F4 which represents the detected electron intensity taken along the line X4 in the image obtained by normalizing the image 41*a*.

The plot F3 agrees well with the line E3, though there are finite differences due to the presence or absence of O atoms. The plot F4 agrees well with the line E4. The values of the plots F3 and F4 are each given as the percentage of the amount of electrons detected by the detector relative to the total amount of electrons incident on the sample.

The lines E1 to E4 in FIG. 15 are the same as the lines E1 to E4 in FIG. 14.

As can be seen from the above results, the normalized reverse image and the normalized bright-field image agree well with the calculated reverse image and the calculated bright-field image, respectively, though there are finite differences due to the presence or absence of O atoms. It has therefore been found that the normalization concept described above is viable.

Next, to verify the normalization concept described above, a difference image between the normalized reverse image of the dark-field image and the normalized bright-field image was obtained by calculation for a plurality of samples.

Figure 16:
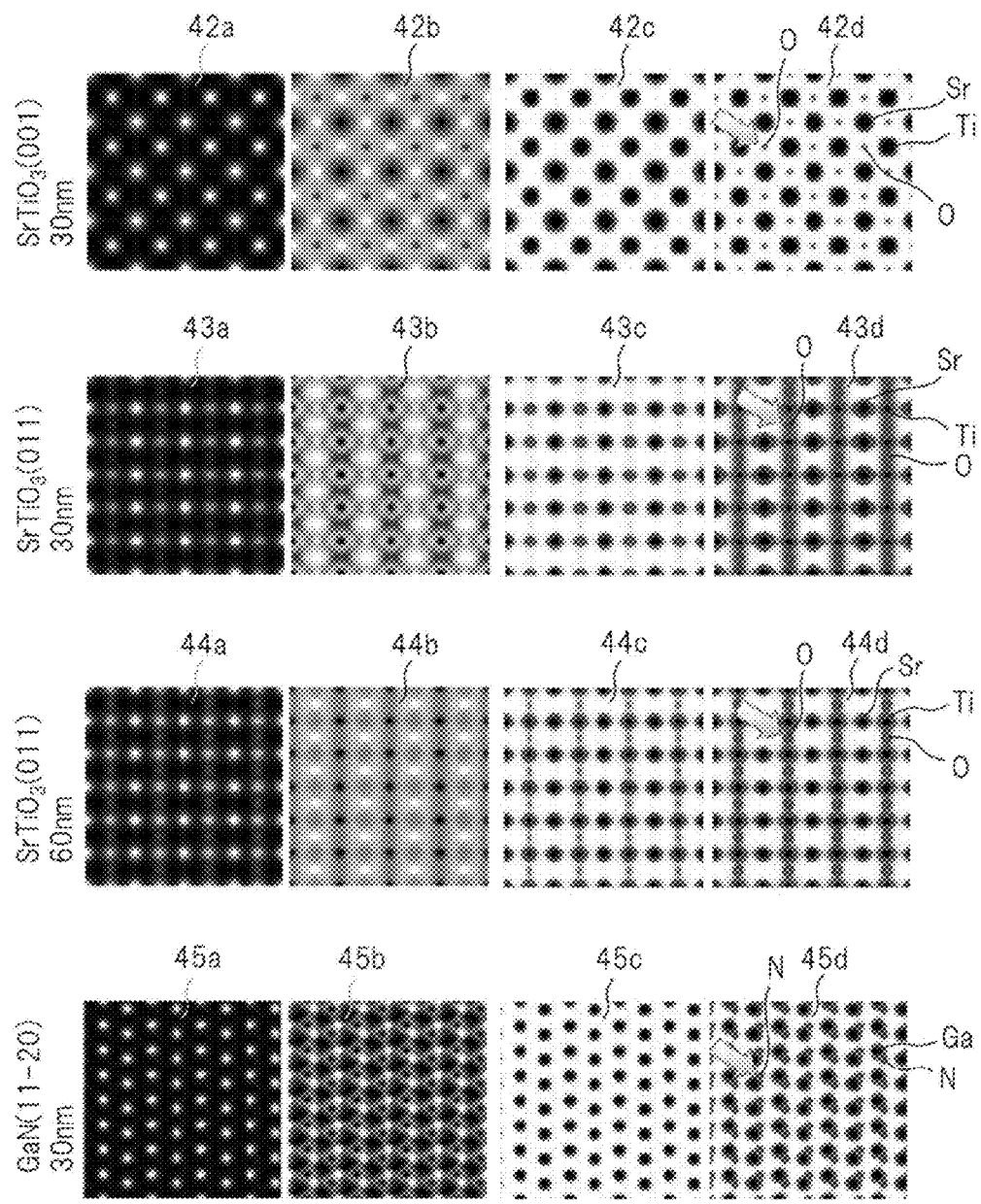
FIG. 16 is a diagram depicting difference images obtained by calculation for a plurality of samples.

FIG. 16 is a diagram depicting difference images obtained by calculation for four samples.

First, images 42*a*, 42*b*, 42*c*, and 42*d* will be described below.

The image 42*a* represents an image obtained by calculating the dark-field image of the (001) plane of SrTiO$_3$ captured using the high-angle annular dark-field image detector 26 depicted in FIGS. 3 and 4. The thickness of the sample was 30 nm. On the other hand, the image 42*b*, which corresponds to the image 42*a*, represents an image obtained by calculating the bright-field image of the (001) plane of SrTiO$_3$ captured using the low-angle bright-field image detector 27 depicted in FIGS. 3 and 4.

The calculation conditions were set as follows: the acceleration voltage was 200 kV, the convergence angle of the electron beam was 20 mrad, the spherical aberration coefficient was −0.5 μm, and the chromatic aberration coefficient was 1.7 mm. The thickness of the sample was 30 nm. The calculations were performed by using a different value for the detection sensitivity of the high-angle annular dark-field image detector 26 than for the detection sensitivity of the low-angle bright-field image detector 27.

The image 42c is an image obtained by normalizing the reverse image generated by reversing the lightness and darkness of the image 42a. The normalization for the reverse image of the image 42a was performed using the calculated reverse image, i.e., the calculated scanning transmission electron micrograph image corresponding to the reverse image of the image 42a. Here, since the crystal structure of the sample was known, the crystal structure of $SrTiO_3$ from which the O atoms had been removed was used as the crystal structure of the sample determined based on the atomic images detected on the dark-field image 42a.

The image 42d is a difference image each of whose pixels has a brightness value equal to the difference between the brightness of the corresponding pixel in the image 42c, i.e., the normalized reverse image of the image 42a, and the brightness of the corresponding pixel in the normalized image 42b. Noise elimination was applied to the image 42d.

In the image 42d, the atomic images of the Sr atoms and Ti atoms as the heavy atoms are both displayed as dark spots. In the image 42d, the atomic images of the O atoms as the light atoms are also displayed as dark spots, as indicated by an arrow in the image.

Next, images 43a, 43b, 43c, and 43d will be described below.

The image 43a represents an image obtained by calculating the dark-field image of the (011) plane of $SrTiO_3$ captured using the high-angle annular dark-field image detector 26 depicted in FIGS. 3 and 4. The thickness of the sample was 30 nm. On the other hand, the image 43b, which corresponds to the image 43a, represents an image obtained by calculating the bright-field image of the (011) plane of $SrTiO_3$ captured using the low-angle bright-field image detector 27 depicted in FIGS. 3 and 4.

The calculation conditions were set as follows: the acceleration voltage was 200 kV, the convergence angle of the electron beam was 20 mrad, the spherical aberration coefficient was −0.5 μm, and the chromatic aberration coefficient was 1.7 mm. The thickness of the sample was 30 nm. The calculations were performed by using a different value for the detection sensitivity of the high-angle annular dark-field image detector 26 than for the detection sensitivity of the low-angle bright-field image detector 27.

The image 43c is an image obtained by normalizing the reverse image generated by reversing the lightness and darkness of the image 43a. The normalization for the reverse image of the image 43a was performed using the calculated reverse image, i.e., the calculated scanning transmission electron micrograph image corresponding to the reverse image of the image 43a. Since the crystal structure of the sample was known, the crystal structure of $SrTiO_3$ from which the O atoms had been removed was used as the crystal structure of the sample determined based on the atomic images detected on the dark-field image 43a.

The image 43d is a difference image each of whose pixels has a brightness value equal to the difference between the brightness of the corresponding pixel in the image 43c, i.e., the normalized reverse image of the image 43a, and the brightness of the corresponding pixel in the normalized image 43b. Noise elimination was applied to the image 43d.

In the image 43d, the atomic images of the Sr atoms and Ti atoms as the heavy atoms are both displayed as dark spots. In the image 43d, the atomic images of the O atoms as the light atoms are also displayed as dark spots, as indicated by an arrow in the image.

Next, images 44a, 44b, 44c, and 44d will be described below.

The image 44a was obtained by calculation in the same manner as the image 43a, except that the thickness of the sample was 60 nm. Likewise, the image 44b corresponds to the image 43b, the image 44c corresponds to the image 43c, and the image 44d corresponds to the image 43d.

In the image 44d, the atomic images of the Sr atoms and Ti atoms as the heavy atoms are both displayed as dark spots. In the image 44d, the atomic images of the O atoms as the light atoms are also displayed as dark spots, as indicated by an arrow in the image.

In this way, even when the thickness of the sample was different, not only the atomic images of the heavy atoms but also the atomic images of the O atoms as the light atoms were observable.

Finally, images 45a, 45b, 45c, and 45d will be described below.

The image 45a represents an image obtained by calculating the dark-field image of the (11-20) plane of GaN captured using the high-angle annular dark-field image detector 26 depicted in FIGS. 3 and 4. The thickness of the sample was 30 nm. On the other hand, the image 45b, which corresponds to the image 45a, represents an image obtained by calculating the bright-field image of the (11-20) plane of GaN captured using the low-angle bright-field image detector 27 depicted in FIGS. 3 and 4.

The calculation conditions were set as follows: the acceleration voltage was 200 kV, the convergence angle of the electron beam was 20 mrad, the spherical aberration coefficient was −0.5 μm, and the chromatic aberration coefficient was 1.7 mm. The thickness of the sample was set to 30 nm. The calculations were performed by using a different value for the detection sensitivity of the high-angle annular dark-field image detector 26 than for the detection sensitivity of the low-angle bright-field image detector 27.

The image 45c is an image obtained by normalizing the reverse image generated by reversing the lightness and darkness of the image 45a. The normalization for the reverse image of the image 45a was performed using the calculated reverse image, i.e., the calculated scanning transmission electron micrograph image corresponding to the reverse image of the image 45a. Since the crystal structure of the sample was known, the crystal structure of GaN from which the N atoms had been removed was used as the crystal structure of the sample determined based on the atomic images detected on the dark-field image 45a.

The image 45d is a difference image each of whose pixels has a brightness value equal to the difference between the brightness of the corresponding pixel in the image 45c, i.e., the normalized reverse image of the image 45a, and the brightness of the corresponding pixel in the normalized image 45b. Noise elimination was applied to the image 45d.

In the image 45d, the atomic images of the Ga atoms as the heavy atoms are displayed as dark spots. In the image 45d, the atomic images of the N atoms as the light atoms are also displayed as dark spots, as indicated by an arrow in the image.

Next, an operational example of the system 10 of the above-described embodiment will be described below with reference to FIG. 17.

Figure 17:
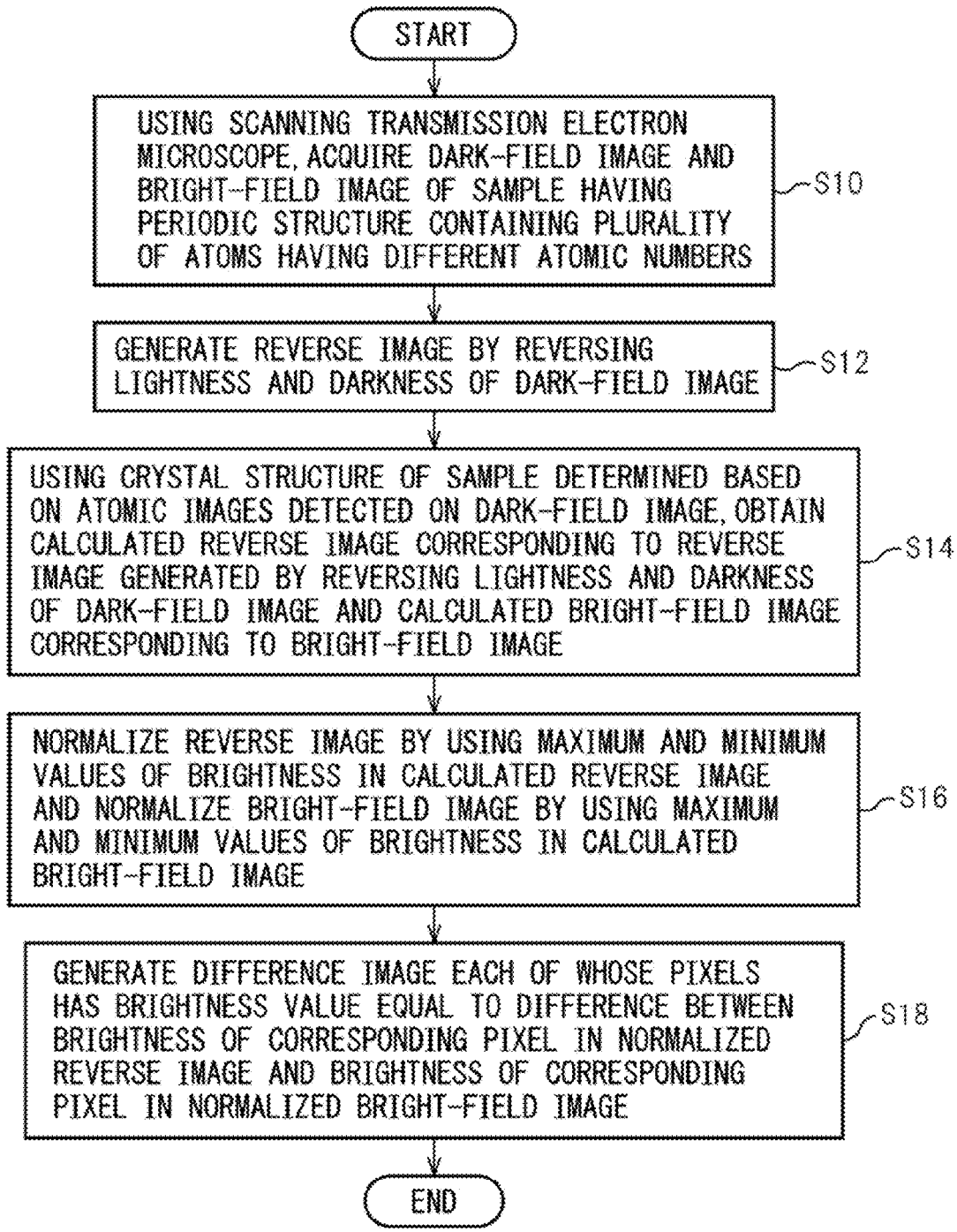
FIG. 17 is a flowchart illustrating an operational example of the system disclosed in this specification.

FIG. 17 is a flowchart illustrating the operational example of the system disclosed in this specification.

First, in step S10, using the scanning transmission electron microscope 20, a dark-field image and a bright-field image are acquired of the sample S which has a periodic structure containing a plurality of atoms having different atomic numbers. The dark-field image is an image captured by detecting, using the high-angle annular dark-field image detector 26, the electrons scattered at angles between the first angle α1 to the optical axis of the scanning transmission electron microscope 20 and the second angle α2 which is larger than the first angle α1. On the other hand, the bright-field image is an image captured along with the dark-field image by detecting, using the low-angle bright-field image detector 27, the electrons scattered within the third angle α3 which is smaller than the first angle α1. The dark-field image and the bright-field image may be acquired in any order or both may be acquired simultaneously.

Next, in step S12, a reverse image is generated by reversing the lightness and darkness of the captured dark-field image.

Next, in step S14, a calculated reverse image corresponding to the reverse image generated by reversing the lightness and darkness of the dark-field image and a calculated bright-field image corresponding to the bright-field image are obtained using the crystal structure of the sample determined based on the atomic images detected on the captured dark-field image. The calculated reverse image and the calculated bright-field image may be acquired in any order or both may be acquired simultaneously.

Next, in step S16, the reverse image is normalized by using the maximum and minimum values of brightness in the calculated reverse image, and the bright-field image is normalized by using the maximum and minimum values of brightness in the calculated bright-field image.

More specifically, the reverse image is normalized so that the maximum and minimum values of brightness in the reverse image agree with the maximum and minimum values of brightness in the calculated reverse image. Likewise, the bright-field image is normalized so that the maximum and minimum values of brightness in the bright-field image agree with the maximum and minimum values of brightness in the calculated bright-field image.

Then, as illustrated in step S18, a difference image is generated each of whose pixels has a brightness value equal to the difference between the brightness of the corresponding pixel in the normalized reverse image and the brightness of the corresponding pixel in the normalized bright-field image.

In the above-described operational example of the system 10, the dark-field image may be normalized first, and then the normalized reverse image may be generated by reversing the lightness and darkness of the normalized dark-field image.

Figure 18:
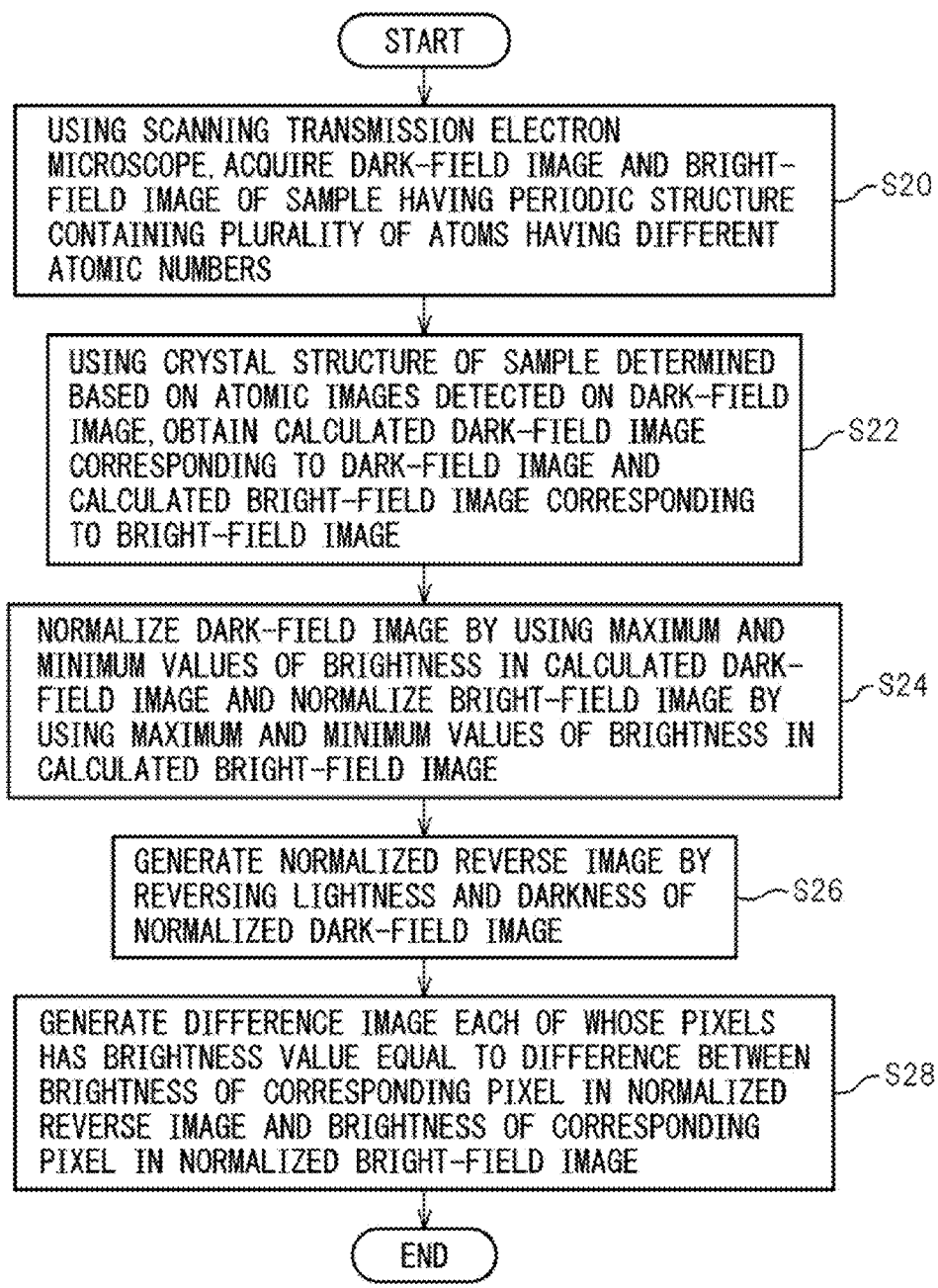
FIG. 18 is a flowchart illustrating another operational example of the system disclosed in this specification.

FIG. 18 is a flowchart illustrating another operational example of the system disclosed in this specification.

First, in step S20, using the scanning transmission electron microscope 20, a dark-field image and a bright-field image are acquired of the sample S which has a periodic structure containing a plurality of atoms having different atomic numbers.

Next, as illustrated in step S22, a calculated dark-field image corresponding to the dark-field image and a calculated bright-field image corresponding to the bright-field image are obtained using the crystal structure of the sample determined based on the atomic images detected on the dark-field image.

Next, as illustrated in step S24, the dark-field image is normalized by using the maximum and minimum values of brightness in the calculated dark-field image, and the bright-field image is normalized by using the maximum and minimum values of brightness in the calculated bright-field image.

More specifically, the dark-field image is normalized so that the maximum and minimum values of brightness in the dark-field image agree with the maximum and minimum values of brightness in the calculated dark-field image. Likewise, the bright-field image is normalized so that the maximum and minimum values of brightness in the bright-field image agree with the maximum and minimum values of brightness in the calculated bright-field image.

Next, as illustrated in step S26, the normalized reverse image is generated by reversing the lightness and darkness of the normalized dark-field image.

Then, as illustrated in step S28, a difference image is generated each of whose pixels has a brightness value equal to the difference between the brightness of the corresponding pixel in the normalized reverse image and the brightness of the corresponding pixel in the normalized bright-field image.

According to the system 10 of the above embodiment, an electron micrograph image is generated that enables both the heavy atoms and light atoms to be observed simultaneously.

The system disclosed in this specification will be further described below with reference to an experimental example. It will, however, be noted that the scope of the present invention is not limited to the following specific experimental example.

$SrTiO_3$ having a (001) plane was used as the sample. The image capturing conditions were set as follows: the acceleration voltage was 200 kV, the convergence angle of the electron beam was 20 mrad, the spherical aberration coefficient was −0.5 μm, and the chromatic aberration coefficient was 1.7 mm. The thickness of the sample was 30 nm.

The first angle α1 was 40 mrad, the second angle α2 was 160 mrad, and the third angle α3 was 9.4 mrad.

Then, images of the (001) plane of $SrTiO_3$ were captured using the high-angle annular dark-field image detector 26 and low-angle bright-field image detector 27 depicted in FIGS. 3 and 4. The captured images are presented in FIG. 19.

The image 46*a* is a dark-field image captured of the (001) plane of $SrTiO_3$ by using the high-angle annular dark-field image detector 26 depicted in FIGS. 3 and 4. The image 46*b* is a bright-field image captured, at the same time as the image 46*a*, of the (001) plane of $SrTiO_3$ by using the low-angle bright-field image detector 27 depicted in FIGS. 3 and 4.

The image 46*c* is a revere image generated by reversing the lightness and darkness of the image 46*a*.

The image 46*d* is a difference image each of whose pixels has a brightness value equal to the difference between the brightness of the corresponding pixel in the image obtained by normalizing the image 46*c* and the brightness of the corresponding pixel in the image obtained by normalizing the image 46*b*. The image 46*c* was normalized using the calculated reverse image, i.e., the calculated scanning transmission electron micrograph image corresponding to the reverse image of the image 46*a* and calculated using the crystal structure of the sample determined based on the atomic images detected on the image 46*a*. Here, since the crystal structure of the sample was known, the crystal structure of $SrTiO_3$ from which the O atoms had been removed was used as the crystal structure of the sample determined based on the atomic images detected on the dark-field image 46*a*. The normalization of the image 46*b* was performed in like manner.

The image 46*f* is an image obtained by eliminating noise from the image 46*d*.

In the image 46*f*, the atomic images of the Sr atoms and Ti atoms as the heavy atoms are both displayed as dark spots. In the image 46*f*, the atomic images of the O atoms as the light atoms are also displayed as dark spots, as indicated by an arrow in the image.

The image 46*e* is an image obtained by eliminating noise from the image 46*c*. Even when noise is eliminated from the image 46*c* which is a revere image generated by reversing the lightness and darkness of the dark-field image 46*a*, only the atomic images of the Sr atoms and Ti atoms as the heavy atoms are displayed as dark spots, and the O atoms as the light atoms are not recognizable.

In the present invention, the image processing apparatus, the image generating method, and the system according to the above embodiment can be modified in various ways without departing from the spirit and scope of the invention.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of superiority and inferiority of the invention. Although the embodiments of the present invention have been described in detail, it should be understood that the various changes, substitutions, and alterations could be made hereto without departing from the spirit and scope of the invention.

What is claimed is:

1. A method comprising:
    acquiring a dark-field image produced by capturing an image of a sample with a scanning transmission electron microscope by detecting electrons scattered at angles between a first angle to an optical axis of the scanning transmission electron microscope and a second angle which is larger than the first angle;
    acquiring a bright-field image captured simultaneously with the dark-field image by detecting electrons scattered within a third angle which is smaller than the first angle;
    generating a reverse image by reversing lightness and darkness of the dark-field image; and
    generating a difference image each of whose pixels has a brightness value equal to a difference between the brightness of a corresponding pixel in the reverse image and the brightness of a corresponding pixel in the bright-field image.

2. The method according to claim 1, wherein the dark-field image and the bright-field image are images captured of the sample which has a periodic structure containing a plurality of atoms having different atomic numbers, the method further comprising:
    obtaining a calculated reverse image as a calculated scanning transmission electron micrograph image corresponding to the reverse image by using a crystal structure of the sample determined based on atomic images detected on the dark-field image;
    obtaining a calculated bright-field image as a calculated scanning transmission electron micrograph image corresponding to the bright-field image by using the determined crystal structure;
    normalizing the reverse image by using the calculated reverse image, while also normalizing the bright-field image by using the calculated bright-field image; and
    generating the difference image each of whose pixels has a brightness value equal to a difference between the brightness of a corresponding pixel in the normalized reverse image and the brightness of a corresponding pixel in the normalized bright-field image.

3. The method according to claim 2, wherein the reverse image is normalized so that maximum and minimum values of brightness in the reverse image agree with maximum and minimum values of brightness in the calculated reverse image, and the bright-field image is normalized so that maximum and minimum values of brightness in the bright-field image agree with maximum and minimum values of brightness in the calculated bright-field image.

4. The method according to claim 1, wherein the dark-field image and the bright-field image are images captured of the sample which has a periodic structure containing a plurality of atoms having different atomic numbers, the method further comprising:
    obtaining a calculated dark-field image as a calculated scanning transmission electron micrograph image corresponding to the dark-field image by using a crystal structure of the sample determined based on atomic images detected on the dark-field image;
    obtaining a calculated bright-field image as a calculated scanning transmission electron micrograph image corresponding to the bright-field image by using the determined crystal structure;
    normalizing the dark-field image by using the calculated dark-field image, while also normalizing the bright-field image by using the calculated bright-field image;
    generating a normalized version of the reverse image by reversing lightness and darkness of the normalized dark-field image; and
    generating the difference image each of whose pixels has a brightness value equal to a difference between the brightness of a corresponding pixel in the normalized reverse image and the brightness of a corresponding pixel in the normalized bright-field image.

5. The method according to claim 4, wherein the dark-field image is normalized so that maximum and minimum values of brightness in the dark-field image agree with maximum and minimum values of brightness in the calculated dark-field image, and the bright-field image is normalized so that maximum and minimum values of brightness in the bright-field image agree with maximum and minimum values of brightness in the calculated bright-field image.

6. The method according to claim 1, wherein the dark-field image is captured with a defocus value that maximizes contrast.

7. The method according to claim 1, wherein the third angle lies within a range of 7 to 12 mrad.

8. An image processing apparatus comprising:
    an input unit which takes as inputs a dark-field image produced by capturing an image of a sample with a scanning transmission electron microscope by detecting electrons scattered at angles between a first angle to an optical axis of the scanning transmission electron microscope and a second angle which is larger than the first angle, and a bright-field image captured simultaneously with the dark-field image by detecting electrons scattered within a third angle which is smaller than the first angle; and
    an image processing unit which generates a reverse image by reversing lightness and darkness of the dark-field image, and generates a difference image each of whose pixels has a brightness value equal to a difference between the brightness of a corresponding pixel in the reverse image and the brightness of a corresponding pixel in the bright-field image.

9. A system comprising:
    a scanning transmission electron microscope which includes
    an electron source which emits an electron beam,
    an objective lens by which the electron beam emitted from the electron source is converged onto a sample,
    a scanning coil, disposed between the electron source and the objective lens, for scanning the electron beam across a surface of the sample,
    a focusing lens by which the electron beam transmitted through the sample is focused to a spot,
    a first detector for detecting electrons scattered at angles between a first angle to an optical axis of the scanning transmission electron microscope and a second angle which is larger than the first angle, a second detector for detecting electrons scattered within a third angle which is smaller than the first angle, and an image generating unit which generates a dark-field image based on a detection signal supplied from the first detector and a bright-field image based on a detection signal supplied from the second detector; and an image processing apparatus which includes an input unit which takes the dark-field image and the bright-field image as inputs, and an image processing unit which generates a reverse image by reversing lightness and darkness of the dark-field image, and generates a difference image each of whose pixels has a brightness value equal to a difference between the brightness of a corresponding pixel in the reverse image and the brightness of a corresponding pixel in the bright-field image.

* * * * *